US009289226B2

(12) United States Patent
Taylor

(10) Patent No.: US 9,289,226 B2
(45) Date of Patent: *Mar. 22, 2016

(54) RETRACTABLE SEPARATING SYSTEMS AND METHODS

(71) Applicant: The Spectranetics Corporation, Colorado Springs, CO (US)

(72) Inventor: Kevin D. Taylor, Colorado Springs, CO (US)

(73) Assignee: The Spectranetics Corporation, Colorado Springs, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 14/589,688

(22) Filed: Jan. 5, 2015

(65) Prior Publication Data

US 2015/0119899 A1 Apr. 30, 2015

Related U.S. Application Data

(63) Continuation of application No. 11/615,006, filed on Dec. 22, 2006, now Pat. No. 8,961,551.

(51) Int. Cl.
*A61B 17/00* (2006.01)
*A61B 17/32* (2006.01)
(Continued)

(52) U.S. Cl.
CPC ... *A61B 17/320016* (2013.01); *A61B 17/32053* (2013.01); *A61B 17/320758* (2013.01);
(Continued)

(58) Field of Classification Search
CPC ............... A61B 17/320016; A61B 17/32053; A61B 17/320758; A61B 2017/00336; A61B 2017/320741; A61B 2017/320024; A61B 2019/4857; A61B 19/54; A61N 1/056; A61N 2001/0578

See application file for complete search history.

(56) References Cited

U.S. PATENT DOCUMENTS 1,663,761 A 3/1928 Johnson
3,400,708 A 9/1968 Scheidt
(Continued)

FOREIGN PATENT DOCUMENTS

JP H05506382 A 9/1993
JP 2004516073 A 6/2004
(Continued)

OTHER PUBLICATIONS

"Horizon Scanning Technology Prioritising Summary: Laser lead extraction systems," Australia and New Zealand Horizon Scanning Network, Aug. 2010, 15 pages.
(Continued)

*Primary Examiner* — Tuan V Nguyen
*Assistant Examiner* — Tin Nguyen
(74) *Attorney, Agent, or Firm* — Faegre Baker Daniels LLP

(57) ABSTRACT

A method for detaching an object from a patient includes providing a tool having a sheath, and a separating assembly operably coupled to a distal end of the sheath. The separating assembly includes a separator moveably coupled to a tip via a threadable connection. The separating assembly is placed near patient tissue that is attached to the object, the sheath is rotated to move the separator distal to the tip, and the separator is applied to the patient tissue that is attached to the object, so as to separate the tissue. A separating system includes a sheath, and a separator threadably coupled with a distal end of the sheath. The separator is adapted to switch between a first configuration where a separating mechanism is deployed, and a second configuration where the separating mechanism is undeployed.

20 Claims, 16 Drawing Sheets

(51) Int. Cl.
*A61B 17/3205* (2006.01)
*A61B 17/3207* (2006.01)
A61B 19/00 (2006.01)
A61N 1/05 (2006.01)

(52) U.S. Cl.
CPC ............... *A61N1/056* (2013.01); *A61B 19/54* (2013.01); *A61B 2017/00336* (2013.01); *A61B 2017/320024* (2013.01); *A61B 2017/320741* (2013.01); *A61B 2019/4857* (2013.01); *A61N 2001/0578* (2013.01)

(56) References Cited

U.S. PATENT DOCUMENTS

| | | | |
|---|---|---|---|
| 3,614,953 A | 10/1971 | Moss | |
| 4,051,596 A | 10/1977 | Hofmann | |
| 4,203,444 A | 5/1980 | Bonnell et al. | |
| 4,246,902 A | 1/1981 | Martinez | |
| 4,274,414 A | 6/1981 | Johnson et al. | |
| D267,145 S | 12/1982 | Kaneko | |
| 4,471,777 A | 9/1984 | McCorkle, Jr. | |
| 4,517,977 A | 5/1985 | Frost | |
| 4,582,056 A | 4/1986 | McCorkle et al. | |
| 4,598,710 A | 7/1986 | Kleinberg et al. | |
| 4,646,738 A | 3/1987 | Trott | |
| 4,662,869 A | 5/1987 | Wright | |
| 4,674,502 A | 6/1987 | Imonti | |
| 4,729,763 A | 3/1988 | Henrie | |
| 4,754,755 A | 7/1988 | Husted | |
| 4,767,403 A | 8/1988 | Hodge | |
| D309,350 S | 7/1990 | Sutherland et al. | |
| 4,943,289 A | 7/1990 | Goode et al. | |
| 4,950,277 A | 8/1990 | Farr | |
| 4,988,347 A | 1/1991 | Goode et al. | |
| 5,011,482 A | 4/1991 | Goode et al. | |
| 5,013,310 A | 5/1991 | Goode et al. | |
| 5,031,634 A | 7/1991 | Simon | |
| 5,152,744 A | 10/1992 | Krause et al. | |
| 5,201,316 A | 4/1993 | Pomeranz et al. | |
| 5,207,683 A | 5/1993 | Goode et al. | |
| 5,261,877 A | 11/1993 | Fine et al. | |
| 5,263,928 A | 11/1993 | Trauthen et al. | |
| 5,275,609 A | 1/1994 | Pingleton et al. | |
| 5,290,275 A | 3/1994 | Kittrell et al. | |
| 5,290,303 A | 3/1994 | Pingleton et al. | |
| 5,383,199 A | 1/1995 | Laudenslager et al. | |
| 5,395,328 A | 3/1995 | Ockuly et al. | |
| 5,423,330 A | 6/1995 | Lee | |
| 5,456,680 A | 10/1995 | Taylor et al. | |
| 5,484,433 A | 1/1996 | Taylor et al. | |
| 5,507,751 A | 4/1996 | Goode et al. | |
| 5,562,694 A | 10/1996 | Sauer et al. | |
| 5,569,284 A | 10/1996 | Young et al. | |
| 5,575,797 A | 11/1996 | Neubauer et al. | |
| 5,620,451 A | 4/1997 | Rosborough | |
| 5,632,749 A | 5/1997 | Goode et al. | |
| 5,651,781 A | 7/1997 | Grace | |
| 5,697,936 A | 12/1997 | Sbipko et al. | |
| 5,718,237 A | 2/1998 | Haaga | |
| 5,725,523 A | 3/1998 | Mueller | |
| 5,766,164 A | 6/1998 | Mueller et al. | |
| 5,782,823 A | 7/1998 | Mueller | |
| 5,807,399 A | 9/1998 | Laske et al. | |
| 5,814,044 A | 9/1998 | Hooven | |
| 5,823,971 A | 10/1998 | Robinson et al. | |
| 5,824,026 A | 10/1998 | Diaz | |
| 5,863,294 A | 1/1999 | Alden | |
| 5,873,886 A | 2/1999 | Larsen et al. | |
| 5,879,365 A | 3/1999 | Whitfield et al. | |
| 5,893,862 A | 4/1999 | Pratt et al. | |
| 5,899,915 A | 5/1999 | Saadat | |
| 5,910,150 A | 6/1999 | Saadat | |
| 5,916,210 A | 6/1999 | Winston | |
| 5,931,848 A | 8/1999 | Saadat | |
| 5,941,893 A | 8/1999 | Saadat | |
| 5,951,581 A | 9/1999 | Saadat et al. | |
| 5,972,012 A | 10/1999 | Ream et al. | |
| 5,980,515 A | 11/1999 | Tu | |
| 5,980,545 A | 11/1999 | Pacala et al. | |
| 6,007,512 A | 12/1999 | Hooven | |
| 6,010,476 A | 1/2000 | Saadat | |
| 6,019,756 A | 2/2000 | Mueller et al. | |
| 6,022,336 A | 2/2000 | Zadno-Azizi et al. | |
| 6,027,497 A | 2/2000 | Daniel et al. | |
| 6,033,402 A | 3/2000 | Tu et al. | |
| 6,036,685 A | 3/2000 | Mueller | |
| 6,051,008 A | 4/2000 | Saadat et al. | |
| 6,066,131 A | 5/2000 | Mueller et al. | |
| 6,080,175 A | 6/2000 | Hogendijk | |
| 6,083,237 A | 7/2000 | Huitema et al. | |
| 6,099,537 A | 8/2000 | Sugai et al. | |
| 6,102,926 A | 8/2000 | Tartaglia et al. | |
| D430,781 S | 9/2000 | Hillegonds | |
| 6,117,149 A | 9/2000 | Sorensen et al. | |
| 6,120,520 A | 9/2000 | Saadat et al. | |
| 6,126,654 A | 10/2000 | Giba et al. | |
| 6,136,005 A | 10/2000 | Goode et al. | |
| 6,139,543 A | 10/2000 | Esch et al. | |
| 6,152,909 A | 11/2000 | Bagaoisan et al. | |
| 6,152,918 A | 11/2000 | Padilla et al. | |
| 6,156,049 A | 12/2000 | Lovato et al. | |
| 6,159,203 A | 12/2000 | Sinofsky | |
| 6,159,225 A | 12/2000 | Makower | |
| 6,162,214 A | 12/2000 | Mueller et al. | |
| 6,165,188 A | 12/2000 | Saadat et al. | |
| 6,167,315 A | 12/2000 | Coe et al. | |
| 6,174,307 B1 | 1/2001 | Daniel et al. | |
| 6,190,352 B1 | 2/2001 | Haarala et al. | |
| 6,190,353 B1 | 2/2001 | Makower et al. | |
| 6,203,537 B1 | 3/2001 | Adrian | |
| 6,210,400 B1 | 4/2001 | Hebert et al. | |
| 6,228,076 B1 | 5/2001 | Winston et al. | |
| 6,235,044 B1 | 5/2001 | Root et al. | |
| 6,241,692 B1 | 6/2001 | Tu et al. | |
| 6,245,011 B1 | 6/2001 | Dudda et al. | |
| 6,251,121 B1 | 6/2001 | Saadat | |
| 6,258,083 B1 | 7/2001 | Daniel et al. | |
| 6,290,668 B1 | 9/2001 | Gregory et al. | |
| 6,315,774 B1 | 11/2001 | Daniel et al. | |
| 6,324,434 B2 | 11/2001 | Coe et al. | |
| 6,379,351 B1 | 4/2002 | Thapliyal et al. | |
| 6,395,002 B1 | 5/2002 | Ellman et al. | |
| 6,398,773 B1 | 6/2002 | Bagaoisan et al. | |
| 6,402,771 B1 | 6/2002 | Palmer et al. | |
| 6,402,781 B1 | 6/2002 | Langberg et al. | |
| 6,419,674 B1 | 7/2002 | Bowser et al. | |
| 6,419,684 B1 | 7/2002 | Heisler et al. | |
| 6,423,051 B1 | 7/2002 | Kaplan et al. | |
| 6,428,539 B1 | 8/2002 | Baxter et al. | |
| 6,428,556 B1 | 8/2002 | Chin | |
| 6,432,119 B1 | 8/2002 | Saadat | |
| 6,436,054 B1 | 8/2002 | Viola et al. | |
| 6,436,114 B1 | 8/2002 | Novak et al. | |
| 6,454,741 B1 | 9/2002 | Muni et al. | |
| 6,454,758 B1 | 9/2002 | Thompson et al. | |
| 6,461,349 B1 | 10/2002 | Elbrecht et al. | |
| 6,478,777 B1 | 11/2002 | Honeck et al. | |
| 6,488,636 B2 | 12/2002 | Bryan et al. | |
| 6,500,182 B2 | 12/2002 | Foster | |
| 6,512,959 B1 | 1/2003 | Gomperz et al. | |
| 6,527,752 B1 | 3/2003 | Bosley et al. | |
| 6,537,314 B2 | 3/2003 | Langberg et al. | |
| 6,540,865 B1 | 4/2003 | Miekka et al. | |
| 6,554,779 B2 | 4/2003 | Viola et al. | |
| 6,558,382 B2 | 5/2003 | Jahns et al. | |
| 6,565,588 B1 | 5/2003 | Clement et al. | |
| 6,569,082 B1 | 5/2003 | Chin | |
| 6,575,997 B1 | 6/2003 | Palmer et al. | |
| 6,592,607 B1 | 7/2003 | Palmer et al. | |
| 6,595,982 B2 | 7/2003 | Sekino et al. | |
| 6,599,296 B1 | 7/2003 | Gillick et al. | |
| 6,602,241 B2 | 8/2003 | Makower et al. | |
| 6,607,547 B1 | 8/2003 | Chin | |

(56) References Cited

U.S. PATENT DOCUMENTS

| | | |
|---|---|---|
| 6,610,046 B1 | 8/2003 | Usami et al. |
| 6,613,013 B2 | 9/2003 | Haarala et al. |
| 6,620,153 B2 | 9/2003 | Mueller et al. |
| 6,620,160 B2 | 9/2003 | Lewis et al. |
| 6,620,180 B1 | 9/2003 | Bays et al. |
| 6,641,590 B1 | 11/2003 | Palmer et al. |
| 6,652,480 B1 | 11/2003 | Imran et al. |
| 6,652,548 B2 | 11/2003 | Evans et al. |
| 6,660,021 B1 | 12/2003 | Palmer et al. |
| 6,663,626 B2 | 12/2003 | Truckai et al. |
| 6,669,685 B1 | 12/2003 | Rizoiu et al. |
| 6,673,090 B2 | 1/2004 | Root et al. |
| 6,687,548 B2 | 2/2004 | Goode |
| 6,702,813 B1 | 3/2004 | Baxter et al. |
| 6,706,018 B2 | 3/2004 | Westlund et al. |
| 6,706,052 B1 | 3/2004 | Chin |
| 6,706,065 B2 | 3/2004 | Langberg et al. |
| 6,709,456 B2 | 3/2004 | Langberg et al. |
| 6,712,773 B1 | 3/2004 | Viola |
| 6,712,826 B2 | 3/2004 | Lui |
| 6,772,014 B2 | 8/2004 | Coe et al. |
| 6,802,838 B2 | 10/2004 | Loeb et al. |
| 6,805,692 B2 | 10/2004 | Muni et al. |
| 6,810,882 B2 | 11/2004 | Langberg et al. |
| 6,818,001 B2 | 11/2004 | Wulfman et al. |
| 6,860,860 B2 | 3/2005 | Viola |
| 6,871,085 B2 | 3/2005 | Sommer |
| 6,884,240 B1 | 4/2005 | Dykes |
| 6,887,238 B2 | 5/2005 | Jahns et al. |
| 6,893,450 B2 | 5/2005 | Foster |
| 6,913,612 B2 | 7/2005 | Palmer et al. |
| 6,962,585 B2 | 11/2005 | Poleo et al. |
| 6,979,290 B2 | 12/2005 | Mourlas et al. |
| 6,979,319 B2 | 12/2005 | Manning et al. |
| 6,989,028 B2 | 1/2006 | Lashinski et al. |
| 6,999,809 B2 | 2/2006 | Currier et al. |
| 7,004,956 B2 | 2/2006 | Palmer et al. |
| 7,011,682 B2 | 3/2006 | Lashinski et al. |
| 7,022,133 B2 | 4/2006 | Yee et al. |
| 7,033,335 B2 | 4/2006 | Haarala et al. |
| 7,033,344 B2 | 4/2006 | Imran |
| 7,033,357 B2 | 4/2006 | Baxter et al. |
| 7,060,061 B2 | 6/2006 | Altshuler et al. |
| 7,063,693 B2 | 6/2006 | Guenst |
| 7,077,856 B2 | 7/2006 | Whitman |
| 7,092,765 B2 | 8/2006 | Geske et al. |
| 7,104,983 B2 | 9/2006 | Grasso et al. |
| 7,114,642 B2 | 10/2006 | Whitman |
| 7,117,039 B2 | 10/2006 | Manning et al. |
| 7,149,587 B2 | 12/2006 | Wardle et al. |
| 7,151,965 B2 | 12/2006 | Osypka |
| 7,189,207 B2 | 3/2007 | Viola |
| 7,191,015 B2 | 3/2007 | Lamson et al. |
| 7,192,430 B2 | 3/2007 | Truckai et al. |
| 7,204,824 B2 | 4/2007 | Moulis |
| 7,214,180 B2 | 5/2007 | Chin |
| 7,226,459 B2 | 6/2007 | Cesarini et al. |
| 7,238,179 B2 | 7/2007 | Brucker et al. |
| 7,238,180 B2 | 7/2007 | Mester et al. |
| 7,252,641 B2 | 8/2007 | Thompson et al. |
| 7,264,587 B2 | 9/2007 | Chin |
| 7,273,478 B2 | 9/2007 | Appling et al. |
| 7,276,052 B2 | 10/2007 | Kobayashi et al. |
| 7,288,096 B2 | 10/2007 | Chin |
| 7,296,577 B2 | 11/2007 | Lashinski et al. |
| 7,306,588 B2 | 12/2007 | Loeb et al. |
| 7,326,226 B2 | 2/2008 | Root et al. |
| 7,328,071 B1 | 2/2008 | Stehr et al. |
| 7,344,546 B2 | 3/2008 | Wulfman et al. |
| 7,357,794 B2 | 4/2008 | Makower et al. |
| 7,359,756 B2 | 4/2008 | Goode |
| 7,369,901 B1 | 5/2008 | Morgan et al. |
| 7,396,354 B2 | 7/2008 | Rychnovsky et al. |
| 7,398,781 B1 | 7/2008 | Chin |
| 7,449,010 B1 | 11/2008 | Hayase et al. |
| 7,462,167 B2 | 12/2008 | Kratz et al. |
| 7,485,127 B2 | 2/2009 | Nistal |
| 7,494,484 B2 | 2/2009 | Beck et al. |
| 7,507,252 B2 | 3/2009 | Lashinski et al. |
| 7,509,169 B2 | 3/2009 | Eigler et al. |
| 7,510,576 B2 | 3/2009 | Langberg et al. |
| 7,513,877 B2 | 4/2009 | Viola |
| 7,513,892 B1 | 4/2009 | Haarala et al. |
| 7,526,342 B2 | 4/2009 | Chin et al. |
| 7,537,602 B2 | 5/2009 | Whitman |
| D594,983 S | 6/2009 | Price et al. |
| 7,540,865 B2 | 6/2009 | Griffin et al. |
| 7,544,197 B2 | 6/2009 | Kelsch et al. |
| 7,559,941 B2 | 7/2009 | Zannis et al. |
| D600,792 S | 9/2009 | Eubanks et al. |
| 7,591,790 B2 | 9/2009 | Pflueger |
| 7,597,698 B2 | 10/2009 | Chin |
| 7,606,615 B2 | 10/2009 | Makower et al. |
| 7,611,474 B2 | 11/2009 | Hibner et al. |
| 7,637,904 B2 | 12/2009 | Wingler et al. |
| 7,645,286 B2 | 1/2010 | Catanese et al. |
| 7,648,466 B2 | 1/2010 | Stephens et al. |
| 7,651,503 B1 | 1/2010 | Coe et al. |
| 7,651,504 B2 | 1/2010 | Goode et al. |
| D610,259 S | 2/2010 | Way et al. |
| D611,146 S | 3/2010 | Way et al. |
| 7,674,272 B2 | 3/2010 | Torrance et al. |
| 7,695,485 B2 | 4/2010 | Whitman et al. |
| 7,695,512 B2 | 4/2010 | Lashinski et al. |
| 7,697,996 B2 | 4/2010 | Manning et al. |
| 7,713,231 B2 | 5/2010 | Wulfman et al. |
| 7,713,235 B2 | 5/2010 | Torrance et al. |
| 7,713,281 B2 | 5/2010 | Leeflang et al. |
| 7,722,549 B2 | 5/2010 | Nakao |
| 7,740,626 B2 | 6/2010 | Takayama et al. |
| 7,743,960 B2 | 6/2010 | Whitman et al. |
| D619,252 S | 7/2010 | Way et al. |
| D619,253 S | 7/2010 | Way et al. |
| 7,758,594 B2 | 7/2010 | Lamson et al. |
| 7,758,613 B2 | 7/2010 | Whitman |
| D621,939 S | 8/2010 | Way et al. |
| 7,766,923 B2 | 8/2010 | Catanese et al. |
| 7,780,682 B2 | 8/2010 | Catanese et al. |
| 7,780,694 B2 | 8/2010 | Palmer et al. |
| 7,794,411 B2 | 9/2010 | Ritchart et al. |
| 7,798,813 B1 | 9/2010 | Harrel |
| 7,803,151 B2 | 9/2010 | Whitman |
| 7,806,835 B2 | 10/2010 | Hibner et al. |
| 7,811,281 B1 | 10/2010 | Rentrop |
| 7,815,655 B2 | 10/2010 | Catanese et al. |
| 7,842,009 B2 | 11/2010 | Torrance et al. |
| 7,845,538 B2 | 12/2010 | Whitman |
| 7,858,038 B2 | 12/2010 | Andreyko et al. |
| D631,155 S | 1/2011 | Peine et al. |
| 7,875,018 B2 | 1/2011 | Tockman et al. |
| 7,875,049 B2 | 1/2011 | Eversull et al. |
| D631,965 S | 2/2011 | Price et al. |
| 7,890,186 B2 | 2/2011 | Wardle et al. |
| 7,890,192 B1 | 2/2011 | Kelsch et al. |
| 7,896,879 B2 | 3/2011 | Solsberg et al. |
| 7,896,891 B2 | 3/2011 | Catanese et al. |
| 7,905,889 B2 | 3/2011 | Catanese et al. |
| 7,909,836 B2 | 3/2011 | McLean et al. |
| 7,914,464 B2 | 3/2011 | Burdorff et al. |
| 7,914,542 B2 | 3/2011 | Lamson et al. |
| D635,671 S | 4/2011 | Way et al. |
| 7,918,230 B2 | 4/2011 | Whitman et al. |
| 7,918,803 B2 | 4/2011 | Ritchart et al. |
| 7,930,040 B1 | 4/2011 | Kelsch et al. |
| 7,935,146 B2 | 5/2011 | Langberg et al. |
| 7,938,786 B2 | 5/2011 | Ritchie et al. |
| 7,942,830 B2 | 5/2011 | Solsberg et al. |
| 7,951,071 B2 | 5/2011 | Whitman et al. |
| 7,951,158 B2 | 5/2011 | Catanese et al. |
| 7,963,040 B2 | 6/2011 | Shan et al. |
| 7,963,433 B2 | 6/2011 | Whitman et al. |
| 7,974,710 B2 | 7/2011 | Seifert |
| 7,981,049 B2 | 7/2011 | Ritchie et al. |
| 7,981,050 B2 | 7/2011 | Ritchart et al. |

(56) References Cited

U.S. PATENT DOCUMENTS

| | | |
|---|---|---|
| 7,981,128 B2 | 7/2011 | To et al. |
| 7,988,726 B2 | 8/2011 | Langberg et al. |
| 7,991,258 B2 | 8/2011 | Temelkuran et al. |
| 7,992,758 B2 | 8/2011 | Whitman et al. |
| 7,993,350 B2 | 8/2011 | Ventura et al. |
| 7,993,351 B2 | 8/2011 | Worley et al. |
| 7,993,359 B1 | 8/2011 | Atwell et al. |
| 8,007,469 B2 | 8/2011 | Duffy |
| 8,007,488 B2 | 8/2011 | Ravenscroft |
| 8,007,503 B2 | 8/2011 | Catanese et al. |
| 8,007,506 B2 | 8/2011 | To et al. |
| 8,016,748 B2 | 9/2011 | Mourlas et al. |
| 8,016,844 B2 | 9/2011 | Privitera et al. |
| 8,016,855 B2 | 9/2011 | Whitman et al. |
| 8,016,858 B2 | 9/2011 | Whitman |
| 8,021,373 B2 | 9/2011 | Whitman et al. |
| 8,025,199 B2 | 9/2011 | Whitman et al. |
| 8,043,309 B2 | 10/2011 | Catanese et al. |
| RE42,959 E | 11/2011 | Saadat et al. |
| 8,052,616 B2 | 11/2011 | Andrisek et al. |
| 8,052,659 B2 | 11/2011 | Ravenscroft et al. |
| 8,056,786 B2 | 11/2011 | Whitman et al. |
| 8,056,791 B2 | 11/2011 | Whitman |
| D650,074 S | 12/2011 | Hunt et al. |
| 8,070,762 B2 | 12/2011 | Escudero et al. |
| 8,090,430 B2 | 1/2012 | Makower et al. |
| 8,097,012 B2 | 1/2012 | Kagarise |
| 8,100,920 B2 | 1/2012 | Gambale et al. |
| 8,118,208 B2 | 2/2012 | Whitman |
| 8,126,570 B2 | 2/2012 | Manning et al. |
| 8,128,577 B2 | 3/2012 | Viola |
| 8,128,636 B2 | 3/2012 | Lui et al. |
| 8,133,214 B2 | 3/2012 | Hayase et al. |
| 8,137,377 B2 | 3/2012 | Palmer et al. |
| 8,142,442 B2 | 3/2012 | Palmer et al. |
| 8,142,446 B2 | 3/2012 | Shan |
| RE43,300 E | 4/2012 | Saadat et al. |
| 8,157,815 B2 | 4/2012 | Catanese et al. |
| 8,186,559 B1 | 5/2012 | Whitman |
| 8,187,204 B2 | 5/2012 | Miller et al. |
| 8,192,430 B2 | 6/2012 | Goode et al. |
| 8,202,229 B2 | 6/2012 | Miller et al. |
| 8,206,409 B2 | 6/2012 | Privitera et al. |
| 8,211,118 B2 | 7/2012 | Catanese et al. |
| 8,216,254 B2 | 7/2012 | McLean et al. |
| 8,235,916 B2 | 8/2012 | Whiting et al. |
| 8,236,016 B2 | 8/2012 | To et al. |
| 8,239,039 B2 | 8/2012 | Zarembo et al. |
| 8,241,272 B2 | 8/2012 | Arnold et al. |
| 8,251,916 B2 | 8/2012 | Speeg et al. |
| 8,252,015 B2 | 8/2012 | Leeflang et al. |
| 8,257,312 B2 | 9/2012 | Duffy |
| 8,272,554 B2 | 9/2012 | Whitman et al. |
| 8,273,078 B2 | 9/2012 | Muenker |
| 8,295,947 B2 | 10/2012 | Lamson et al. |
| 8,303,511 B2 | 11/2012 | Eigler et al. |
| 8,323,240 B2 | 12/2012 | Wulfman et al. |
| 8,326,437 B2 | 12/2012 | Cully et al. |
| 8,333,740 B2 | 12/2012 | Shippert |
| 8,333,776 B2 | 12/2012 | Cheng et al. |
| 8,337,516 B2 | 12/2012 | Escudero et al. |
| 8,343,167 B2 | 1/2013 | Henson |
| 8,343,187 B2 | 1/2013 | Lamson et al. |
| 8,353,899 B1 | 1/2013 | Wells et al. |
| 8,361,094 B2 | 1/2013 | To et al. |
| 8,364,280 B2 | 1/2013 | Marnfeldt et al. |
| 8,372,098 B2 | 2/2013 | Tran |
| D679,010 S | 3/2013 | Kitayama et al. |
| 8,394,110 B2 | 3/2013 | Catanese et al. |
| 8,394,113 B2 | 3/2013 | Wei et al. |
| 8,425,535 B2 | 4/2013 | McLean et al. |
| D687,549 S | 8/2013 | Johnson et al. |
| D697,618 S | 1/2014 | Gonzales et al. |
| D706,928 S | 6/2014 | Harrison et al. |
| D708,742 S | 7/2014 | Dallemagne et al. |
| 2001/0005789 A1 | 6/2001 | Root et al. |
| 2001/0016717 A1 | 8/2001 | Haarala et al. |
| 2001/0025174 A1 | 9/2001 | Daniel et al. |
| 2001/0031981 A1 | 10/2001 | Evans et al. |
| 2001/0039427 A1 | 11/2001 | Dinger et al. |
| 2001/0041899 A1 | 11/2001 | Foster |
| 2001/0044568 A1 | 11/2001 | Langberg et al. |
| 2002/0002372 A1 | 1/2002 | Jahns et al. |
| 2002/0007204 A1 | 1/2002 | Goode |
| 2002/0010475 A1 | 1/2002 | Lui |
| 2002/0010487 A1 | 1/2002 | Evans et al. |
| 2002/0016628 A1 | 2/2002 | Langberg et al. |
| 2002/0045811 A1 | 4/2002 | Kittrell et al. |
| 2002/0065543 A1 | 5/2002 | Gomperz et al. |
| 2002/0068954 A1 | 6/2002 | Foster |
| 2002/0087151 A1 | 7/2002 | Mody et al. |
| 2002/0103477 A1 | 8/2002 | Grasso et al. |
| 2002/0103532 A1 | 8/2002 | Langberg et al. |
| 2002/0103533 A1 | 8/2002 | Langberg et al. |
| 2002/0123785 A1 | 9/2002 | Zhang et al. |
| 2002/0151961 A1 | 10/2002 | Lashinski et al. |
| 2002/0183735 A1 | 12/2002 | Edwards et al. |
| 2002/0188278 A1 | 12/2002 | Tockman et al. |
| 2003/0009146 A1 | 1/2003 | Muni et al. |
| 2003/0036788 A1 | 2/2003 | Coe et al. |
| 2003/0050630 A1 | 3/2003 | Mody et al. |
| 2003/0050631 A1 | 3/2003 | Mody et al. |
| 2003/0055444 A1 | 3/2003 | Evans et al. |
| 2003/0055445 A1 | 3/2003 | Evans et al. |
| 2003/0069575 A1 | 4/2003 | Chin et al. |
| 2003/0073985 A1 | 4/2003 | Mueller et al. |
| 2003/0078562 A1 | 4/2003 | Makower et al. |
| 2003/0105451 A1 | 6/2003 | Westlund et al. |
| 2003/0125619 A1 | 7/2003 | Manning et al. |
| 2003/0167056 A1 | 9/2003 | Jahns et al. |
| 2003/0187460 A1 | 10/2003 | Chin et al. |
| 2003/0187461 A1 | 10/2003 | Chin |
| 2003/0199916 A1 | 10/2003 | Yee et al. |
| 2003/0199921 A1 | 10/2003 | Palmer et al. |
| 2003/0204202 A1 | 10/2003 | Palmer et al. |
| 2003/0208209 A1 | 11/2003 | Gambale et al. |
| 2003/0229323 A1 | 12/2003 | Haarala et al. |
| 2003/0229353 A1 | 12/2003 | Cragg |
| 2004/0006358 A1 | 1/2004 | Wulfman et al. |
| 2004/0010248 A1 | 1/2004 | Appling et al. |
| 2004/0015193 A1 | 1/2004 | Lamson et al. |
| 2004/0019359 A1 | 1/2004 | Worley et al. |
| 2004/0049208 A1 | 3/2004 | Hill et al. |
| 2004/0054368 A1 | 3/2004 | Truckai et al. |
| 2004/0054388 A1 | 3/2004 | Osypka |
| 2004/0059348 A1 | 3/2004 | Geske et al. |
| 2004/0064024 A1 | 4/2004 | Sommer |
| 2004/0068256 A1 | 4/2004 | Rizoiu et al. |
| 2004/0068288 A1 | 4/2004 | Palmer et al. |
| 2004/0093016 A1 | 5/2004 | Root et al. |
| 2004/0102804 A1 | 5/2004 | Chin |
| 2004/0102841 A1 | 5/2004 | Langberg et al. |
| 2004/0111101 A1 | 6/2004 | Chin |
| 2004/0116939 A1 | 6/2004 | Goode |
| 2004/0133220 A1 | 7/2004 | Lashinski et al. |
| 2004/0138562 A1 | 7/2004 | Makower et al. |
| 2004/0138744 A1 | 7/2004 | Lashinski et al. |
| 2004/0143284 A1 | 7/2004 | Chin |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0153096 A1 | 8/2004 | Goode et al. |
| 2004/0153098 A1 | 8/2004 | Chin et al. |
| 2004/0172116 A1 | 9/2004 | Seifert et al. |
| 2004/0176840 A1 | 9/2004 | Langberg et al. |
| 2004/0181249 A1 | 9/2004 | Torrance et al. |
| 2004/0216748 A1 | 11/2004 | Chin |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0235611 A1 | 11/2004 | Nistal |
| 2004/0236312 A1 | 11/2004 | Nistal et al. |
| 2004/0236397 A1 | 11/2004 | Coe et al. |
| 2004/0243123 A1 | 12/2004 | Grasso et al. |

(56) References Cited

U.S. PATENT DOCUMENTS

| | | |
|---|---|---|
| 2004/0243162 A1 | 12/2004 | Wulfman et al. |
| 2004/0254534 A1 | 12/2004 | Bjorkman et al. |
| 2004/0260322 A1 | 12/2004 | Rudko et al. |
| 2004/0267276 A1 | 12/2004 | Camino et al. |
| 2004/0267304 A1 | 12/2004 | Zannis et al. |
| 2005/0004644 A1 | 1/2005 | Kelsch et al. |
| 2005/0025798 A1 | 2/2005 | Moulis |
| 2005/0027337 A1 | 2/2005 | Rudko et al. |
| 2005/0038419 A9 | 2/2005 | Arnold et al. |
| 2005/0054948 A1 | 3/2005 | Goldenberg |
| 2005/0060030 A1 | 3/2005 | Lashinski et al. |
| 2005/0065561 A1 | 3/2005 | Manning et al. |
| 2005/0090748 A1 | 4/2005 | Makower et al. |
| 2005/0096740 A1 | 5/2005 | Langberg et al. |
| 2005/0131399 A1 | 6/2005 | Loeb et al. |
| 2005/0149104 A1 | 7/2005 | Leeflang et al. |
| 2005/0149105 A1 | 7/2005 | Leeflang et al. |
| 2005/0197623 A1 | 9/2005 | Leeflang et al. |
| 2005/0222607 A1 | 10/2005 | Palmer et al. |
| 2005/0228402 A1 | 10/2005 | Hofmann |
| 2005/0228452 A1 | 10/2005 | Mourlas et al. |
| 2005/0251116 A1 | 11/2005 | Steinke et al. |
| 2005/0259942 A1 | 11/2005 | Temelkuran et al. |
| 2005/0267557 A1 | 12/2005 | Flynn et al. |
| 2005/0273090 A1 | 12/2005 | Nieman et al. |
| 2005/0283143 A1 | 12/2005 | Rizoiu |
| 2005/0288596 A1 | 12/2005 | Eigler et al. |
| 2005/0288604 A1 | 12/2005 | Eigler et al. |
| 2005/0288654 A1 | 12/2005 | Nieman et al. |
| 2006/0041250 A1 | 2/2006 | Poleo |
| 2006/0052660 A1 | 3/2006 | Chin |
| 2006/0084839 A1 | 4/2006 | Mourlas et al. |
| 2006/0100663 A1 | 5/2006 | Palmer et al. |
| 2006/0116746 A1 | 6/2006 | Chin |
| 2006/0116757 A1 | 6/2006 | Lashinski et al. |
| 2006/0167417 A1 | 7/2006 | Kratz et al. |
| 2006/0173440 A1 | 8/2006 | Lamson et al. |
| 2006/0217755 A1 | 9/2006 | Eversull et al. |
| 2006/0229490 A1 | 10/2006 | Chin |
| 2006/0235431 A1 | 10/2006 | Goode et al. |
| 2006/0247751 A1 | 11/2006 | Seifert |
| 2006/0253179 A1 | 11/2006 | Goode et al. |
| 2006/0265042 A1 | 11/2006 | Catanese et al. |
| 2006/0276871 A1 | 12/2006 | Lamson et al. |
| 2006/0287574 A1 | 12/2006 | Chin |
| 2007/0015964 A1 | 1/2007 | Eversull et al. |
| 2007/0016130 A1 | 1/2007 | Leeflang et al. |
| 2007/0021812 A1 | 1/2007 | Manning et al. |
| 2007/0049929 A1 | 3/2007 | Catanese et al. |
| 2007/0050003 A1 | 3/2007 | Zarembo et al. |
| 2007/0083217 A1 | 4/2007 | Eversull et al. |
| 2007/0100410 A1 | 5/2007 | Lamson et al. |
| 2007/0106328 A1 | 5/2007 | Wardle et al. |
| 2007/0129710 A1 | 6/2007 | Rudko et al. |
| 2007/0142846 A1 | 6/2007 | Catanese et al. |
| 2007/0197861 A1 | 8/2007 | Reiley et al. |
| 2007/0198020 A1 | 8/2007 | Reiley et al. |
| 2007/0232981 A1 | 10/2007 | Ravenscroft et al. |
| 2007/0276412 A1 | 11/2007 | Catanese et al. |
| 2007/0293853 A1 | 12/2007 | Truckai et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0015625 A1 | 1/2008 | Ventura et al. |
| 2008/0021484 A1 | 1/2008 | Catanese et al. |
| 2008/0021485 A1 | 1/2008 | Catanese et al. |
| 2008/0033232 A1 | 2/2008 | Catanese et al. |
| 2008/0033456 A1 | 2/2008 | Catanese et al. |
| 2008/0033458 A1 | 2/2008 | McLean et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039876 A1 | 2/2008 | Catanese et al. |
| 2008/0039889 A1 | 2/2008 | Lamson et al. |
| 2008/0039893 A1 | 2/2008 | McLean et al. |
| 2008/0039894 A1 | 2/2008 | Catanese et al. |
| 2008/0045986 A1 | 2/2008 | To et al. |
| 2008/0051756 A1 | 2/2008 | Makower et al. |
| 2008/0058759 A1 | 3/2008 | Makower et al. |
| 2008/0071341 A1 | 3/2008 | Goode et al. |
| 2008/0071342 A1 | 3/2008 | Goode et al. |
| 2008/0097426 A1 | 4/2008 | Root et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0125748 A1 | 5/2008 | Patel |
| 2008/0147061 A1 | 6/2008 | Goode et al. |
| 2008/0154293 A1 | 6/2008 | Taylor |
| 2008/0154296 A1 | 6/2008 | Taylor et al. |
| 2008/0183163 A1 | 7/2008 | Lampropoulos et al. |
| 2008/0208105 A1 | 8/2008 | Zelickson et al. |
| 2008/0221560 A1 | 9/2008 | Arai et al. |
| 2008/0228208 A1 | 9/2008 | Wulfman et al. |
| 2008/0249516 A1 | 10/2008 | Muenker |
| 2008/0262516 A1 | 10/2008 | Gambale et al. |
| 2008/0275497 A1 | 11/2008 | Palmer et al. |
| 2008/0275498 A1 | 11/2008 | Palmer et al. |
| 2008/0281308 A1 | 11/2008 | Neuberger et al. |
| 2008/0287888 A1 | 11/2008 | Ravenscroft |
| 2008/0306333 A1 | 12/2008 | Chin |
| 2009/0012510 A1 | 1/2009 | Bertolero et al. |
| 2009/0018523 A1 | 1/2009 | Lamson et al. |
| 2009/0018553 A1 | 1/2009 | McLean et al. |
| 2009/0034927 A1 | 2/2009 | Temelkuran et al. |
| 2009/0036871 A1 | 2/2009 | Hayase et al. |
| 2009/0054918 A1 | 2/2009 | Henson |
| 2009/0060977 A1 | 3/2009 | Lamson et al. |
| 2009/0071012 A1 | 3/2009 | Shan et al. |
| 2009/0076522 A1 | 3/2009 | Shan |
| 2009/0131907 A1 | 5/2009 | Chin et al. |
| 2009/0157045 A1 | 6/2009 | Haarala et al. |
| 2009/0192439 A1 | 7/2009 | Lamson et al. |
| 2009/0204128 A1 | 8/2009 | Lamson et al. |
| 2009/0221994 A1 | 9/2009 | Neuberger et al. |
| 2009/0222025 A1 | 9/2009 | Catanese et al. |
| 2009/0227999 A1 | 9/2009 | Willis et al. |
| 2009/0234378 A1 | 9/2009 | Escudero et al. |
| 2009/0270862 A1 | 10/2009 | Arcenio |
| 2010/0004606 A1 | 1/2010 | Hansen et al. |
| 2010/0030154 A1 | 2/2010 | Duffy |
| 2010/0030161 A1 | 2/2010 | Duffy |
| 2010/0030262 A1 | 2/2010 | McLean et al. |
| 2010/0030263 A1 | 2/2010 | Cheng et al. |
| 2010/0049225 A1 | 2/2010 | To et al. |
| 2010/0063488 A1 | 3/2010 | Fischer et al. |
| 2010/0125253 A1 | 5/2010 | Olson et al. |
| 2010/0137873 A1 | 6/2010 | Grady et al. |
| 2010/0160952 A1 | 6/2010 | Leeflang et al. |
| 2010/0191165 A1 | 7/2010 | Appling et al. |
| 2010/0198194 A1 | 8/2010 | Manning et al. |
| 2010/0198229 A1 | 8/2010 | Olomutzki et al. |
| 2010/0217081 A1 | 8/2010 | Deppmeier et al. |
| 2010/0217277 A1 | 8/2010 | Truong |
| 2010/0222737 A1 | 9/2010 | Arnold et al. |
| 2010/0222787 A1 | 9/2010 | Goode et al. |
| 2010/0240951 A1 | 9/2010 | Catanese et al. |
| 2010/0256616 A1 | 10/2010 | Katoh et al. |
| 2010/0280496 A1 | 11/2010 | Shippert |
| 2010/0324472 A1 | 12/2010 | Wulfman |
| 2010/0331793 A1 | 12/2010 | Tulleken |
| 2011/0004238 A1 | 1/2011 | Palmer et al. |
| 2011/0009957 A1 | 1/2011 | Langberg et al. |
| 2011/0022057 A1 | 1/2011 | Eigler et al. |
| 2011/0028959 A1 | 2/2011 | Chasan |
| 2011/0034790 A1 | 2/2011 | Mourlas et al. |
| 2011/0040238 A1 | 2/2011 | Wulfman et al. |
| 2011/0040312 A1 | 2/2011 | Lamson et al. |
| 2011/0040315 A1 | 2/2011 | To et al. |
| 2011/0040326 A1 | 2/2011 | Wei et al. |
| 2011/0046648 A1 | 2/2011 | Johnston et al. |

(56) References Cited

U.S. PATENT DOCUMENTS

| | | |
|---|---|---|
| 2011/0054493 A1 | 3/2011 | McLean et al. |
| 2011/0060349 A1 | 3/2011 | Cheng et al. |
| 2011/0071440 A1 | 3/2011 | Torrance et al. |
| 2011/0105947 A1 | 5/2011 | Fritscher-Ravens et al. |
| 2011/0106004 A1 | 5/2011 | Eubanks et al. |
| 2011/0106099 A1 | 5/2011 | Duffy et al. |
| 2011/0112548 A1 | 5/2011 | Fifer et al. |
| 2011/0112562 A1 | 5/2011 | Torrance |
| 2011/0112563 A1 | 5/2011 | To et al. |
| 2011/0112564 A1 | 5/2011 | Wolf |
| 2011/0118660 A1 | 5/2011 | Torrance et al. |
| 2011/0144423 A1 | 6/2011 | Tong et al. |
| 2011/0144425 A1 | 6/2011 | Catanese et al. |
| 2011/0151463 A1 | 6/2011 | Wulfman |
| 2011/0152607 A1 | 6/2011 | Catanese et al. |
| 2011/0152906 A1 | 6/2011 | Escudero et al. |
| 2011/0152907 A1 | 6/2011 | Escudero et al. |
| 2011/0160747 A1 | 6/2011 | McLean et al. |
| 2011/0160748 A1 | 6/2011 | Catanese et al. |
| 2011/0166564 A1 | 7/2011 | Merrick et al. |
| 2011/0178543 A1 | 7/2011 | Chin et al. |
| 2011/0190758 A1 | 8/2011 | Lamson et al. |
| 2011/0196298 A1 | 8/2011 | Anderson et al. |
| 2011/0196355 A1 | 8/2011 | Mitchell et al. |
| 2011/0208207 A1 | 8/2011 | Bowe et al. |
| 2011/0213398 A1 | 9/2011 | Chin et al. |
| 2011/0218528 A1 | 9/2011 | Ogata et al. |
| 2011/0238078 A1 | 9/2011 | Goode et al. |
| 2011/0238102 A1 | 9/2011 | Gutfinger et al. |
| 2011/0245751 A1 | 10/2011 | Hofmann |
| 2011/0257592 A1 | 10/2011 | Ventura et al. |
| 2011/0270169 A1 | 11/2011 | Gardeski et al. |
| 2011/0270170 A1 | 11/2011 | Gardeski et al. |
| 2011/0270289 A1 | 11/2011 | To et al. |
| 2011/0300010 A1 | 12/2011 | Jarnagin et al. |
| 2011/0301417 A1 | 12/2011 | Mourlas et al. |
| 2011/0301626 A1 | 12/2011 | To et al. |
| 2012/0029278 A1 | 2/2012 | Sato et al. |
| 2012/0035590 A1 | 2/2012 | Whiting et al. |
| 2012/0041422 A1 | 2/2012 | Whiting et al. |
| 2012/0053564 A1 | 3/2012 | Ravenscroft |
| 2012/0065659 A1 | 3/2012 | To |
| 2012/0083810 A1 | 4/2012 | Escudero et al. |
| 2012/0083826 A1 | 4/2012 | Chao et al. |
| 2012/0095447 A1 | 4/2012 | Fojtik |
| 2012/0095479 A1 | 4/2012 | Bowe et al. |
| 2012/0097174 A1 | 4/2012 | Spotnitz et al. |
| 2012/0123411 A1 | 5/2012 | Ibrahim et al. |
| 2012/0136341 A1 | 5/2012 | Appling et al. |
| 2012/0165827 A1 | 6/2012 | Khairkhahan et al. |
| 2012/0165861 A1 | 6/2012 | Palmer et al. |
| 2012/0191015 A1 | 7/2012 | Zannis et al. |
| 2012/0209173 A1 | 8/2012 | Hayase et al. |
| 2012/0215305 A1 | 8/2012 | Le et al. |
| 2012/0239008 A1 | 9/2012 | Fojtik |
| 2012/0245600 A1 | 9/2012 | McLean et al. |
| 2012/0253229 A1 | 10/2012 | Cage |
| 2012/0265183 A1 | 10/2012 | Tulleken et al. |
| 2012/0323252 A1 | 12/2012 | Booker |
| 2012/0323253 A1 | 12/2012 | Garai et al. |
| 2012/0330292 A1 | 12/2012 | Shadduck et al. |
| 2013/0006228 A1 | 1/2013 | Johnson et al. |
| 2013/0035676 A1 | 2/2013 | Mitchell et al. |
| 2013/0096582 A1 | 4/2013 | Cheng et al. |
| 2013/0103047 A1 | 4/2013 | Steingisser et al. |
| 2015/0105796 A1 | 4/2015 | Grace |
| 2015/0196297 A1 | 7/2015 | (Prommersberger) Stopek |
| 2015/0305744 A1 | 10/2015 | Moore et al. |

FOREIGN PATENT DOCUMENTS

| | | |
|---|---|---|
| WO | 9117711 A1 | 11/1991 |
| WO | 9533513 A1 | 12/1995 |
| WO | 9907295 A1 | 2/1999 |
| WO | 9949937 A1 | 10/1999 |
| WO | 9958066 A1 | 11/1999 |
| WO | 0176680 A1 | 10/2001 |
| WO | 02049690 A9 | 5/2003 |
| WO | 2004049956 A2 | 6/2004 |
| WO | 2004080345 A2 | 9/2004 |
| WO | 2004080507 A2 | 9/2004 |
| WO | 2006007410 A2 | 1/2006 |
| WO | 2008005888 A2 | 1/2008 |
| WO | 2008005891 A2 | 1/2008 |
| WO | 2008042987 A2 | 4/2008 |
| WO | 2009005779 A1 | 1/2009 |
| WO | 2009054968 A1 | 4/2009 |
| WO | 2009065082 A1 | 5/2009 |
| WO | 2009126309 A2 | 10/2009 |
| WO | 2011003113 A1 | 1/2011 |
| WO | 2011084863 A2 | 7/2011 |
| WO | 2011133941 A2 | 10/2011 |
| WO | 2011162595 A1 | 12/2011 |
| WO | 2012009697 A4 | 4/2012 |
| WO | 2012098335 A1 | 7/2012 |
| WO | 2012114333 A1 | 8/2012 |
| WO | 2012177117 A1 | 12/2012 |
| WO | 2013036588 A1 | 3/2013 |
| WO | 2014151814 A1 | 9/2014 |

OTHER PUBLICATIONS

Decision to Grant for European Patent Application No. 07255018.9, dated Aug. 8, 2013, 2 pages.

EP extended Search Report mailed Oct. 21, 2009; Application No. 07255019.7, 8 pages.

Extended European Search Report for European Application No. 07255018.9, dated Nov. 12, 2010.

Final Action for U.S. Appl. No. 11/615,005, mailed Nov. 9, 2009, 10 pages.

Final Action for U.S. Appl. No. 11/615,005, mailed Nov. 21, 2013, 20 pages.

Intent to Grant for European Patent Application No. 07255018.9, dated Nov. 29, 2012, 7 pages.

International Search Report and Written Opinion for International Patent Application No. PCT/US2013/059434, dated Dec. 13, 2013, 14 pages.

Notice of Allowance for European Patent Application No. 07255018. 9, dated Jul. 26, 2012, 47 pages.

Notice of Allowance for Japan Patent Application No. 2007-333273, mailed Jan. 16, 2014, 3 pages.

Official Action for European Patent Application No. 07255018.9, dated Jul. 19, 2011, 3 pages.

Official Action for U.S. Appl. No. 11/615,005, mailed Apr. 16, 2009, 13 pages.

Official Action for U.S. Appl. No. 11/615,005, mailed Feb. 11, 2011, 12 pages.

Official Action for U.S. Appl. No. 11/615,005, mailed Jul. 21, 2010, 10 pages.

Official Action for U.S. Appl. No. 11/615,005, mailed Mar. 14, 2013, 16 pages.

Official Action for U.S. Appl. No. 13/800,728, mailed Jan. 16, 2014, 14 pages.

Official Action with English translation for Japan Patent Application No. 2007-333173, mailed Apr. 30, 2013, 5 pages.

Official Action with English translation for Japan Patent Application No. 2007-333173, mailed Aug. 13, 2012, 7 pages.

Official Action with English translation for Japan Patent Application No. 2007-333273, mailed Jul. 30, 2012, 7 pages.

Official Action with English translation for Japan Patent Application No. 2007-333273, mailed Jun. 6, 2013, 10 pages.

U.S. Appl. No. 13/800,651, Hendrick et al., filed Mar. 13, 2013, 69 pages.

U.S. Appl. No. 13/800,675, Hendrick et al., filed Mar. 13, 2013, 68 pages.

U.S. Appl. No. 13/800,700, Hendrick et al., filed Mar. 13, 2013, 68 pages.

U.S. Appl. No. 13/800,728, Hendrick et al., filed Mar. 13, 2013, 68 pages.

(56) References Cited

OTHER PUBLICATIONS

U.S. Appl. No. 13/828,231, Bowe et al., filed Mar. 14, 2013, 89 pages.
U.S. Appl. No. 13/828,310, Bowe et al., filed Mar. 14, 2013, 90 pages.
U.S. Appl. No. 13/828,383, Bowe et al., filed Mar. 14, 2013, 86 pages.
U.S. Appl. No. 13/828,441, Bowe et al., filed Mar. 14, 2013, 86 pages.
U.S. Appl. No. 13/828,536, Hendrick et al., filed Mar. 14, 2013, 41 pages.
U.S. Appl. No. 13/828,638, Fiser, filed Mar. 14, 2013, 52 pages.
U.S. Appl. No. 13/834,405, Grace et al., filed Mar. 15, 2013, 79 pages.
Department of Health and Ageing in Australian Government, "Horizon Scanning Technology Prioritising: Laser Extraction Systems." 2010. 15 pages.
International Search Report and Written Opinion issued in PCT/US2014/021167 mailed Jun. 26, 2014, 19 pages.
International Search Report and Written Opinion issued in PCT/US2014/026496 mailed Jul. 30, 2014, 16 pages.
International Search Report and Written Opinion issued in PCT/US2015/016899, mailed May 1, 2015, 14 pages.
International Search Report and Written Opinion issued in PCT/US2015/018305, mailed May 28, 2015, 14 pages.
PCT Application No. PCT/US2015/016899 entitled Medical Device for Removing an Implanted Object filed Feb. 20, 2015.
PCT Application No. PCT/US2015/018305 entitled Multiple Configuration Surgical Cutting Device filed Mar. 2, 2015.
U.S. Appl. No. 14/577,976 entitled Surgical Instrument Including an Inwardly Deflecting Cutting Tip for Removing an Implanted Object filed Dec. 19, 2014.
U.S. Appl. No. 14/589,688 entitled Retractable Separating Systems and Methods filed Jan. 5, 2015.
U.S. Appl. No. 14/627,851 entitled Medical Device for Removing an Implanted Object filed Feb. 20, 2015.
U.S. Appl. No. 14/627,950 entitled Medical Device for Removing an Implanted Object filed Feb. 20, 2015.
U.S. Appl. No. 14/635,742 entitled Multiple Configuration Surgical Cutting Device filed Mar. 2, 2015.
U.S. Appl. No. 14/725,781 entitled Surgical Instrument for Removing an Implanted Object, filed May 29, 2015.
Design U.S. Appl. No. 29/519,239 entitled Medical Device Handle, filed Mar. 3, 2015.
Design U.S. Appl. No. 29/519,258 entitled Medical Device Handle, filed Mar. 3, 2015.
U.S. Appl. No. 61/793,597 entitled Surgical Instrument for Removing an Implanted Object filed Mar. 15, 2013.
U.S. Appl. No. 61/987,993 entitled Dual Mode Mechanical Catheter Cutting System filed May 2, 2014.
U.S. Appl. No. 62/005,315 entitled Surgical Instrument for Removing an Implanted Object filed May 30, 2014.
U.S. Appl. No. 62/058,790 entitled Medical Device for Removing an Implanted Object filed Oct. 2, 2014.
U.S. Appl. No. 62/094,808 entitled Multiple Configuration Surgical Cutting Device filed Dec. 19, 2014.
U.S. Appl. No. 62/113,865 entitled Medical Device for Removing an Implanted Object filed Feb. 9, 2015.

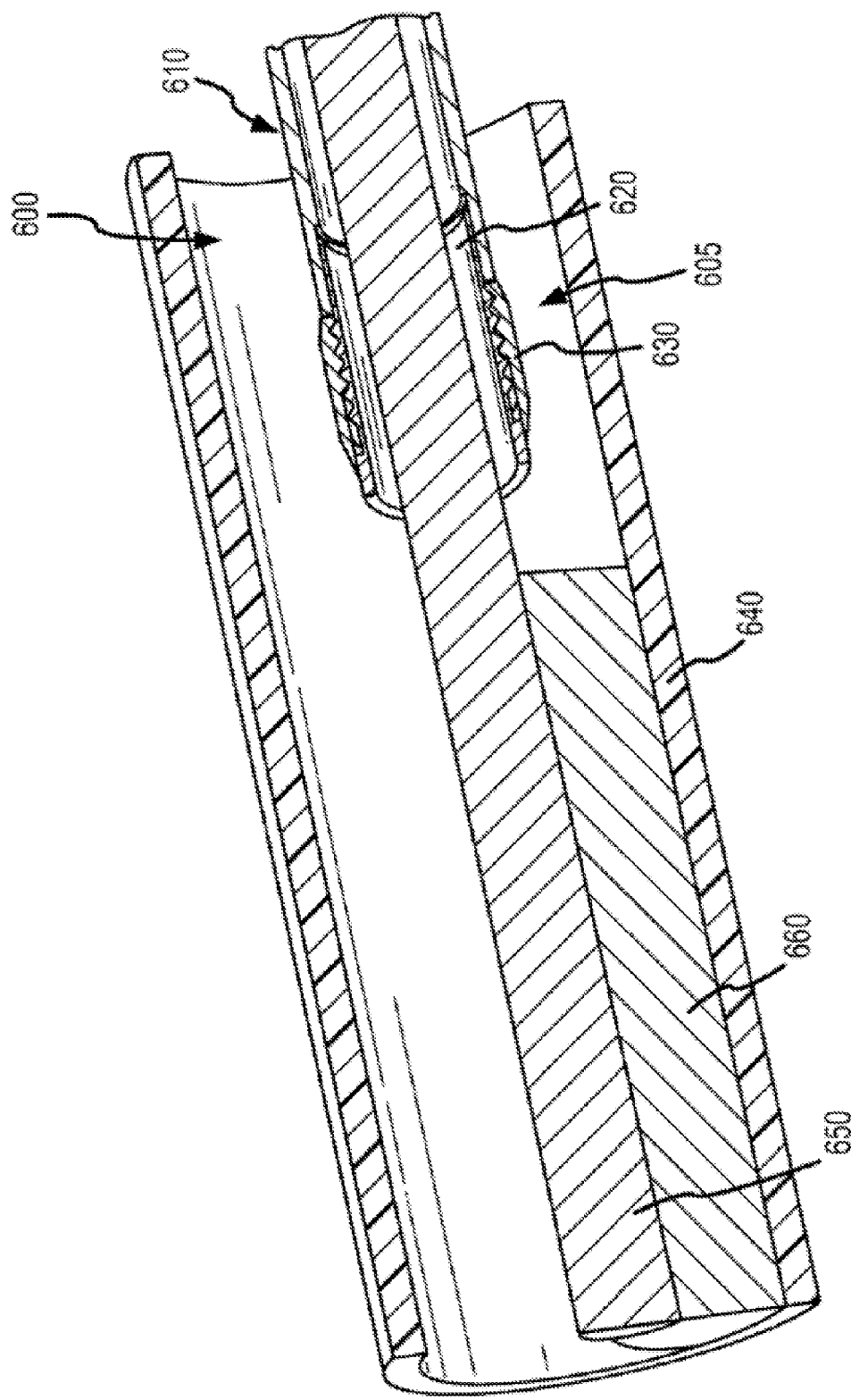

RETRACTABLE SEPARATING SYSTEMS AND METHODS

CROSS-REFERENCES TO RELATED APPLICATIONS

This application is a continuation of U.S. patent application Ser. No. 11/615,006, filed Dec. 22, 2006, now U.S. Pat. No. 8,961,551 and titled RETRACTABLE SEPARATING SYSTEMS AND METHODS, the entire contents of which are incorporated herein by reference for all purposes. This application is also related to U.S. patent application Ser. No. 11/615,005, filed Dec. 22, 2006, now U.S. Pat. No. 9,028,520 and titled TISSUE SEPARATING SYSTEMS AND METHODS, the entire contents of which are incorporated herein by reference for all purposes.

BACKGROUND OF THE INVENTION

The present application relates generally to systems and methods for separating an object from tissue in a patient, and more specifically, to techniques for removing pacing leads from a patient.

Cardiac pacing systems typically include a pacemaker and a pacing lead, which are placed inside the body of a patient. The pacemaker includes a power source and circuitry configured to send timed electrical pulses to the pacing lead. The pacing lead carries the electrical pulse to the heart to initiate a heartbeat, and transmits information about the heart's electrical activity to the pacemaker. The pacing lead can include a fixation mechanism that holds the lead to the cardiac tissue. In some cases, a pacing lead is inserted through a vein and guided into a heart chamber where it is attached with the heart. In other instances, a pacing lead is attached to the outside of the heart. A common problem associated with pacing leads is the development of scar tissue or adhesions where the pacing lead contacts the patient's body tissue. Patient tissue can become attached with the pacing lead, and thus removal or extraction of the pacing lead may present complications.

Current pacing lead extraction techniques include mechanical traction, mechanical devices, and laser devices. Mechanical traction is often accomplished by inserting a locking stylet into the lead and pulling to remove it. In some cases, for example where mechanical traction is ineffective, dilating telescopic sheaths can be used to strip away the scar tissue adhering the lead to the body. Unfortunately, metal sheaths that are currently used to strip scar tissue from implanted leads often cannot traverse the tortuous lead path, and in many instances can only be used in proximal locations. Currently used plastic sheaths may be able to access certain distal lead locations, but often suffer from poor torque properties, low radiopacity, and ineffective penetration into hard tissue because they have soft tips that deform when in contact with the hard tissue. Dilation techniques often involve pushing tissue away from the lead when the sheath is pushed longitudinally along the lead. However, longitudinal forces can be easily lost during the procedure by tortuousity or curvature in the lead and by friction encountered within the anatomy or over the pacing lead. Longitudinal forces also may require heavy counter traction on the lead-that can result in pacing lead breakage. Some mechanical sheaths have proposed trigger mechanisms for extending a blade from a sheath. At least some of these devices, however, involve complicated activation mechanisms and may not be well suited for negotiating the tortuous paths present in certain vascular or physiological environments. Laser devices typically employ laser energy to cut the scar tissue away from the lead thus allowing for removal. Although effective in some circumstances for removing chronic implanted pacing leads, many laser systems can be expensive and unaffordable to many treatment centers.

What is needed are improved mechanical devices and methods for extracting pacing leads as well as other objects. These techniques can provide effective alternatives to currently used dilating lead extraction sheaths and laser systems.

BRIEF SUMMARY OF THE INVENTION

Advantageously, embodiments of the present invention encompass cutting, stripping, and dilating device having designs unique in their simplicity. An exemplary separating system involves a minimum number of parts, for example a retractable assembly and an inexpensive low profile flexible sheath that easily tracks over a pacing lead. Mechanical sheath and retractable assembly embodiments can be safely deployed within the vascular system of a patient. For example, a torqueable and flexible polymer sheath can be coupled with a 2-piece tip section that houses a cutting, stripping, or dilating element. The element can be deployed or exposed to separate tissue by rotating the sheath in one direction. Conversely, the element can be retracted back into the tip by rotating the sheath in the other direction. The penetration action of the sheath can be accomplished by rotation of the sheath to minimize force on the lead and vascular system.

In a first aspect, embodiments of the present invention provide a method for separating an object from a patient. The method can include providing a tool that includes a sheath having a proximal end and a distal end, and a separating assembly operably coupled to the distal end of the sheath. The separating assembly can include a tip and a separator having a separating mechanism, and the separating mechanism of the separator can be undeployed. The method can also include placing the separating assembly near patient tissue that is attached to the object, rotating the sheath to induce relative rotational movement between the separator and the tip so as to deploy the separating means of the separator, and applying the deployed separating mechanism to the patient tissue that is attached to the object, so as to separate the tissue from the object. In some cases, rotation of the sheath induces rotational movement of the separator relative to the tip. In some cases, rotation of the sheath induces rotational movement of the tip relative to the separator. The method may also include engaging a contact region of the separating assembly with a site adjacent to or on the patient tissue. In some cases, the contact region is disposed on the separator. In some cases, the contact region is disposed on the tip. Rotation of the sheath may induce relative movement between the tip and the separator via a threaded, a slot and key, or a cam connection that couples the tip and the separator. The object can include a pacing lead, a wire, a catheter, an implant, or the like. In some cases, the patient tissue includes scar tissue. The method may also include visualizing a marker disposed on the separating assembly under fluoroscopy. In some aspects, rotating the sheath includes engaging the proximal end of the sheath. The separating assembly can include a cutting assembly, a dilating assembly, or a stripping assembly. The separator can include a cutter, a dilator, or a stripper. The separating mechanism can include a cutting mechanism, a dilating mechanism, or a stripping mechanism. In some cases, the separating mechanism includes a blade. In some aspects, the method may also include rotating the sheath to induce relative rotational movement between the separator and the tip so as to undeploy the separating mechanism of the separator.

In another aspect, embodiments of the present invention provide a separating system for detaching an object from a patient. The separating system may include a sheath having a distal end, and a separating assembly coupled with the distal end of the sheath. The separating assembly can include a tip and a separator having a separating mechanism or means. The separating assembly may be adapted to switch between a deployed configuration where a portion of the separating mechanism or means is exposed and an undeployed configuration where the portion of the separating mechanism or means is unexposed. The distal end of the sheath may be fixable relative to the tip. Relatedly, the distal end of the sheath may be fixable relative to the separator. In some cases, the separator and the tip are coupled via a threaded, a slot and key, or a cam connection. The separator and tip may be configured for relative rotational movement. The system may also include a contact region. The contact region can be disposed on the separator and adapted to releasably fix the separator relative to the patient. In some cases, the contact region is disposed on the tip and adapted to releasably fix the tip relative to the patient. The contact region may include a sand blasted surface, a grooved surface, a coated surface, a knurled surface, a holed surface, a pitted surface, a notched surface, or the like. In a deployed configuration, the separating mechanism may extend past the tip a distance in the range from about 0.5 mm to about 5 mm. In some aspects, the separating assembly includes a cutting assembly, a dilating assembly, or a stripping assembly. A separator may include a cutter, a dilator, or a stripper. A separating mechanism may include a cutting mechanism, a dilating mechanism, or a stripping mechanism. In some cases, a separating mechanism or means includes a blade.

In another aspect, embodiments of the present invention provide a method for detaching an object from a patient. The method may include, for example, providing a tool that includes a sheath having a proximal end and a distal end, and a separating assembly coupled with the distal end of the sheath. The separating assembly may include a tip and a separator having a separating mechanism, and the separating assembly may be in an undeployed configuration. The method may also include placing the separating assembly near patient tissue that is attached to the object, frictionally engaging a contact region of the separating assembly with a site adjacent to or on the patient tissue, rotating the sheath so as to deploy the separating assembly while the contact region remains frictionally engaged with the site adjacent to or on the patient tissue, and applying the separating mechanism to the patient tissue that is attached to the object, so as to separate the tissue from the object. The contact region can include a sand blasted surface, a grooved surface, a coated surface, a knurled surface, a holed surface, a pitted surface, and a notched surface. Frictionally engaging the contact region with the site can include forcing the region against or contacting the region to the site. In some cases, the method may also include rotating the sheath so as to undeploy the separating assembly.

In another aspect, the present invention provides a method for detaching an object from a patient. The method includes providing a tool comprising a sheath having a proximal end and a distal end, and a cutting assembly operably coupled to the distal end, wherein the cutting assembly comprises a cutter moveably coupled to a tip, and wherein the cutter is flush with or positioned proximal to the tip. The cutter can be linked or coupled with the tip via a threadable connection, a key and groove connection, a cam connection, and the like. The method also includes placing the cutting assembly near patient tissue that is attached to the object, rotating the sheath to move the cutter to a position that is distal to the tip, and applying the cutter to the patient tissue that is attached to the object, so as to cut the tissue. In some cases, the method also includes engaging a contact region of the cutting assembly with a site adjacent to the patient tissue. The contact region can be disposed on the cutter. Relatedly, the contact region can be disposed on the tip. In some cases, rotation of the sheath causes movement of a threaded portion of the tip relative to a threaded portion of the cutter. In some cases, rotation of the sheath causes movement of a threaded portion of the cutter relative to a threaded portion of the tip. Any of a variety of objects, including pacing leads, wires, catheters, implants, and the like, can be removed with this method. In some aspects, the patient tissue includes scar tissue. The method may also include visualizing a marker disposed on the cutting assembly.

In another aspect, embodiments of the present invention provide a cutting system for detaching an object from a patient. The system can include a sheath having a distal end, and a cutting assembly coupled with the distal end of the sheath. The cutting assembly can include a tip engaged with a cutter. The cutter can be coupled with the tip via a threadable connection, a key and groove connection, a cam connection, and the like. The cutting assembly can be adapted to switch between a deployed configuration where the cutter is positioned distal to the tip, and an undeployed configuration where the cutter is flush with or positioned proximal to the tip. In some cases, the distal end of the sheath is fixable relative to the tip. In some cases, the cutter includes an internal lumen, and the tip is disposed at least partially within the internal lumen of the cutter. The cutter may also include a contact region adapted to releasably fix the cutter relative to the patient. The cutter contact region can include a sand blasted surface, a grooved surface, a coated surface, a knurled surface, holes, pits, notches, and the like. In some aspects, the distal end of the sheath is fixable relative to the cutter. The tip may include an internal lumen, and the cutter can be disposed at least partially within the internal lumen of the tip. In some case, the tip includes a contact region adapted to releasably fix the tip relative to the patient. The tip contact region can include a sand blasted surface, a grooved surface, a coated surface, a knurled surface, holes, pits, notches, and the like. When in a deployed configuration the cutter can extend past the tip a distance, for example, in the range from about 0.5 mm to about 5 mm. In another aspect, embodiments of the present invention provide a cutting system for detaching an object from a patient. The cutting system includes a sheath having a distal end, and a cutter threadably coupled with the distal end of the sheath. The cutter can be adapted to switch between a deployed configuration where the cutter is positioned distal to a tip of the distal end, and an undeployed configuration where the cutter is flush with or positioned proximal to the tip.

For a fuller understanding of the nature and advantages of the present invention, reference should be had to the ensuing detailed description taken in conjunction with the accompanying drawings.

BRIEF DESCRIPTION OF THE DRAWINGS

FIGS. 6A-6C illustrate a process for separating a tissue with a separating system, according to embodiments of the present invention.

DETAILED DESCRIPTION OF THE INVENTION

Embodiments of the present invention provide a mechanical sheath and separating tip that can be safely deployed within the vascular system of a patient. A separating system can include, for example, a flexible sheath coupled with a separating assembly, which includes a separator and a tip. The separator can be advanced distally beyond the tip by rotating the sheath in one direction. Conversely, the separator can be retracted back into the tip by rotating the sheath in the other direction. The penetration action of the sheath can be accomplished by rotation of the sheath to minimize force on the lead and vascular system.

Figure 1:
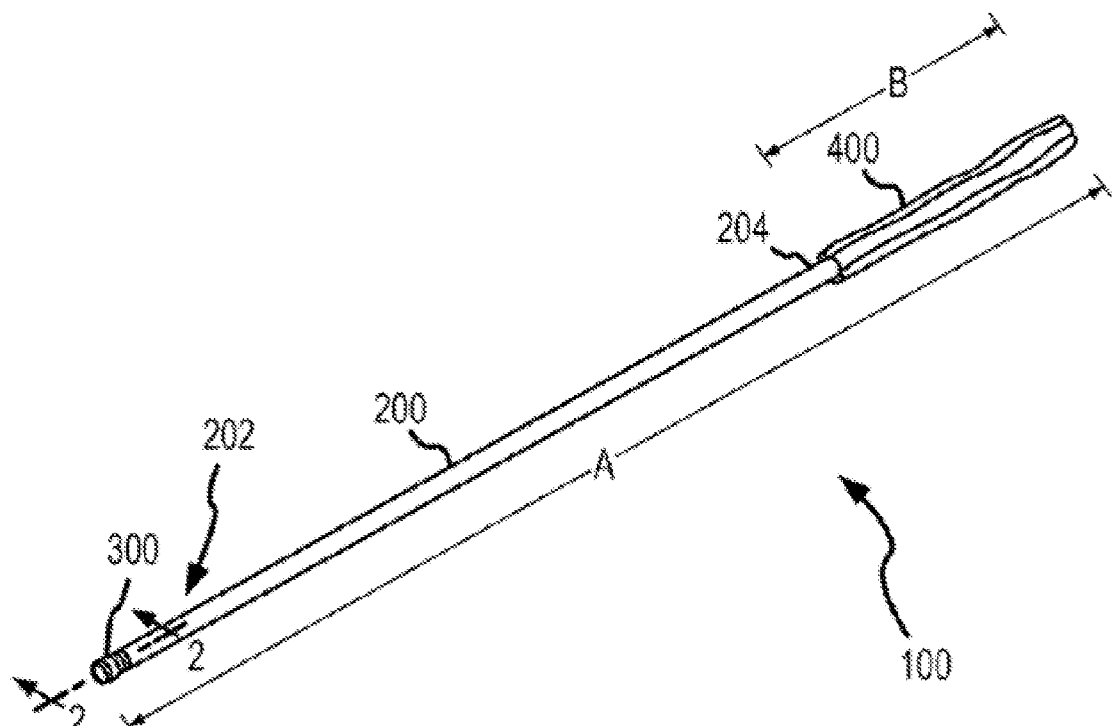
FIG. 1 shows a separating system according to embodiments of the present invention.

Turning now to the drawings, FIG. 1 shows a separating system or tool 100 according to one embodiment of the present invention. Separating or cutting system 100 includes a sheath 200, a separating assembly 300, and a handle 400. In some embodiments, sheath 200 includes or is manufactured from a flexible polymer such as Pebax® or Teflon®, and may also include a stainless steel braid reinforcement. Sheath 200 may include a distal end 202 coupled with separating assembly 300, and a proximal end 204 coupled with handle 400. An operator can use handle 400 to facilitate rotation of sheath 200 and components of separating assembly 300. In some cases, separating system 100 can have a length A within a range from about 25 cm to about 75 cm. Optionally, separating system 100 can a length A that is about 50 cm. In some cases, handle 400 can have a length B within a range from about 4 cm to about 15 cm. Optionally, handle 400 can a length B that is about 8 cm. Exemplary sheath or shaft 200 configurations are further described in previously incorporated U.S. patent application Ser. No. 11/615,005, filed Dec. 22, 2006 (Tissue Separating Systems and Methods).

Figure 2:
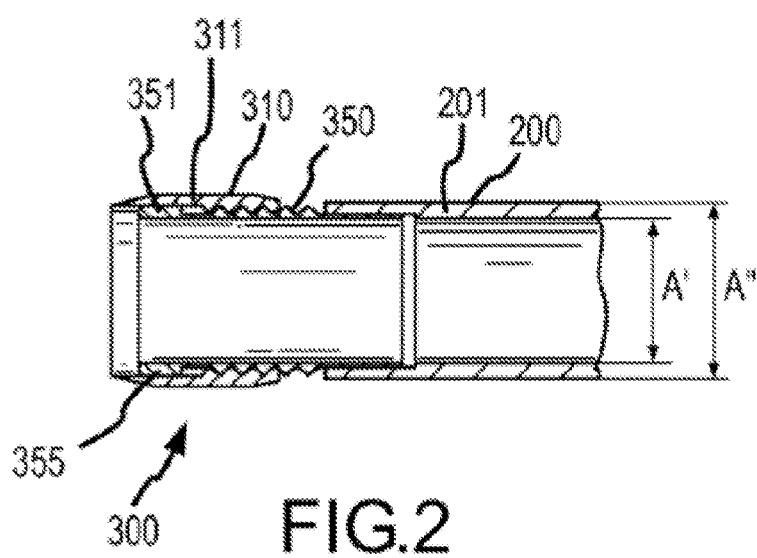
FIG. 2 shows a separating assembly according to embodiments of the present invention.

As depicted in FIG. 2, separating assembly 300 can include a separator 310 in operative association with a tip 350. For example, separator 310 and tip 350 can be coupled via a threaded connection. Some of the embodiments described herein refer to cutting elements, cutting assemblies, cutters, and the like, which often include items for cutting tissue, however it is understood that these cutting features can be replaced with or referred to as stripping or dilating elements, stripping or dilating assemblies, or strippers or dilators. Stripping features can include items for stripping tissue from pacing leads and other objects within the body of a patient. Relatedly, dilating features can include items for dilating tissue surrounding or near pacing leads and other objects within the body of a patient. Cutting features or procedures can be used or referred to interchangeably with stripping features or procedures, and with dilating features or procedures. Methods that include stripping or dilating tissue may or may not include cutting tissue. In some embodiments, cutting, stripping, or dilating elements or procedures, or any combinations thereof, may be referred to as separating elements or procedures. For example, a separator may refer to or encompass a cutter, a stripper, or a dilator, or any combination thereof.

In some embodiments, sheath 200 is integral with tip 350, such that tip 350 represents a distal end of sheath 200. In some embodiments, a distal end of sheath 200 is fixed with tip 350. A separating assembly may include a marker or other detectable feature that can be imaged. For example, a separating system may include a tip marker 351, a separator marker 311, or a sheath marker 201, or any combination thereof. Such markers may include a radiopaque or other imageable material to allow an operator to determine the relative positional relationships of the separating system components. In some cases, separating system components can be constructed of radiopaque material or alternatively plated with a thin coat of highly radiopaque material such as gold. In one embodiment, a tip marker includes a radiopaque material that allows the operator to distinguish when the separator is extended under fluoroscopy. When placed within a vessel or lumen of a patient, separating assembly 300 is typically disposed in an undeployed configuration, whereby a distal end of separator 310 is flush with or proximal to a distal end of tip 350, or otherwise undeployed or unexposed. In some embodiments, an undeployed configuration can refer to a separating assembly having an unexposed separator blade or a non-separating profile. Once the assembly 300 is positioned at or near a tissue which an operator wishes to separate, the operator can maneuver the assembly 300 so that an external surface of separator 310 frictionally contacts a tissue surface of the patient. The operator can then rotate shaft 200 so that tip 350 rotates relative to separator 310, thus extending a portion of separator 310 distally beyond tip 350. The separating assembly 300 is thus in a deployed configuration and ready for separating the desired tissue. In some embodiments, a deployed configuration can refer to a separating assembly having an exposed separator blade or separating means or mechanism, or presenting a separating profile. In some embodiments, sheath 200 has an inner diameter A' within a range from about 0.090 to about 0.200 inches and an outer diameter A" within a range from about 0.130 to about 0.250 inches. Similarly, handle 400 can have an inner diameter within a range from about 0.130 to about 0.250 inches, and an outer diameter within a range from about 0.250 to about 0.750 inches.

Figure 3A:
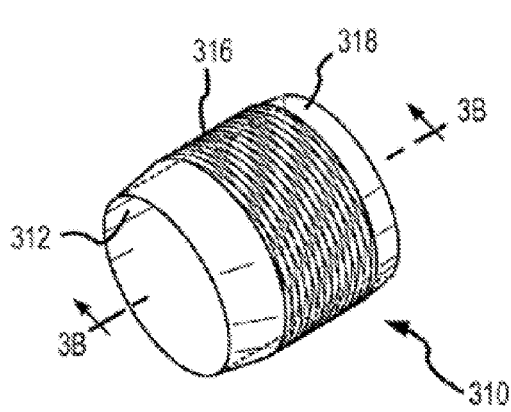
FIGS. 3A-3E show a separator according to embodiments of the present invention.
Figure 3B:
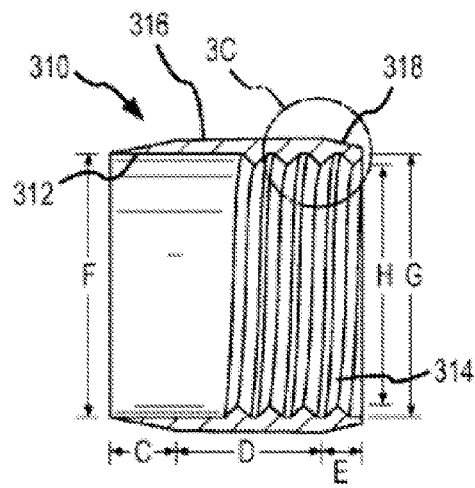
Figure 3C:
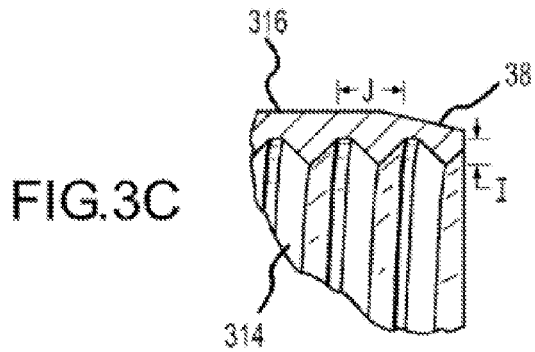
Figure 3D:
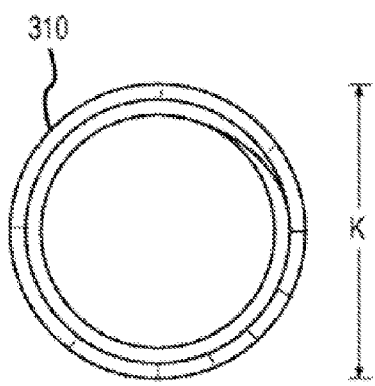
Figure 3E:
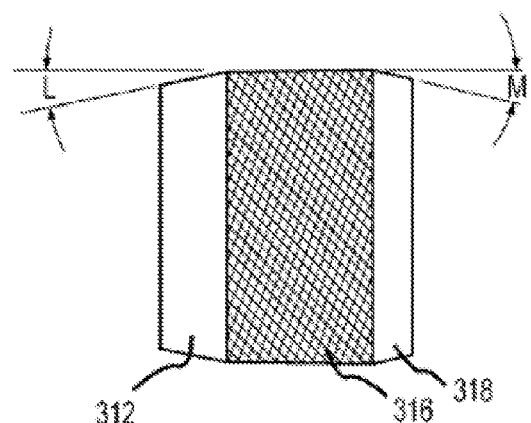

Various features of separator 310 are depicted in FIGS. 3A-3E. For example, as illustrated in FIG. 3A, separator 310 can include a distal separating edge 312, a contact region 316, and a proximal edge 318. Contact region 316 may be disposed at any suitable location on separator 310. For example, contact region 316 can be located at a proximal portion of separator 310, a medial portion of separator 310, or at a distal portion, edge, or face of separator 310. In some cases, as shown in FIG. 3B, distal separating edge 312 can have a length C within a range from about 0.01 inch to about 0.10 inch. Optionally, distal separating edge 312 can have a length C of about 0.05 inch. In some embodiments, exterior contact region 316 can have a length D within a range from about 0.06 inch to about 0.16 inch. Optionally, exterior contact region 316 can have a length D of about 0.11 inch. In some cases, proximal edge 318 can have a length E within a range of about 0.01 inch to about 0.05 inch. Optionally, proximal edge 318 can have a length E of about 0.03 inch. In some cases, distal separating edge 312 can have an interior diameter F within a range of about 0.099 inch to about 0.299 inch. Optionally, distal separating edge 312 can have an interior diameter F of about 0.199 inch. In some embodiments, an internal threaded section 314 can have a major thread diameter G within a range from about 0.1 inch to about 0.3 inch. Optionally, major thread diameter G can be about 0.2 inch. In some embodiments, threaded section 314 can have a minor thread diameter H within a range from about 0.08 inch to about 0.28 inch. Optionally, minor thread diameter H can be about 0.18 inch. As illustrated in FIG. 3C, threaded section 314 can define a thread depth I and a thread pitch J. In some cases, thread depth I can be within a range from about 0.005 inch to about 0.015 inch. Optionally, thread depth I can be about 0.010 inch. In some cases, thread pitch J can be within a range from about 0.010 inch to about 0.030 inch. Optionally, thread pitch J can be about 0.020 inch. In some cases, threaded section 314 can have a thread count within a range from about 10 threads per inch to about 60 threads per inch. Optionally, threaded section 314 can have a thread count of about 40 threads per inch. As depicted in FIG. 3D, cutter 310 can have an outer diameter K within a range from about 0.12 inch to about 0.32 inch. Optionally, outer diameter K can be about 0.22 inch. As shown in FIG. 3E, distal cutting edge 312 and contact region 316 can define a bevel angle L, and contact region 316 and proximal edge 318 can define a bevel angle M. In some cases, bevel angle L can be within a range from about 11.1° to about 15.1°, and bevel angle M can be within a range from about 8.2° to about 12.2°. Optionally, bevel angle L can be about 13.1° and bevel angle M can be about 10.2°.

Figure 4A:
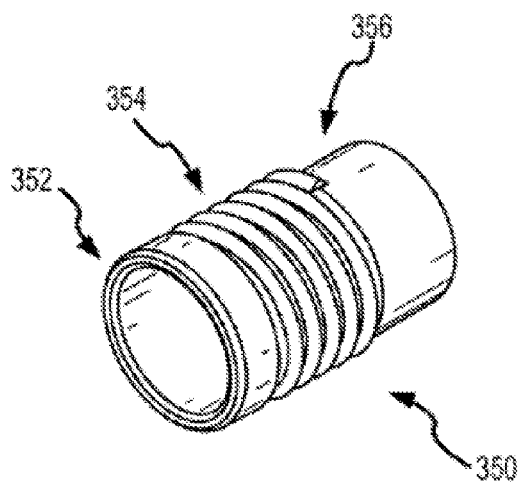
FIGS. 4A-4D show a tip according to embodiments of the present invention.
Figure 4B:
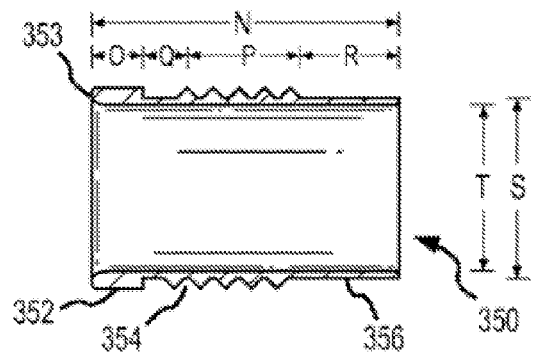
Figure 4C:
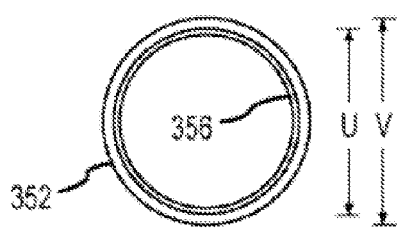
Figure 4D:
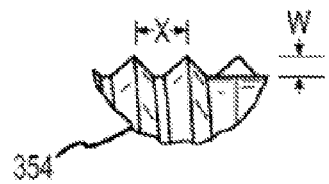

Various features of tip 350 are depicted in FIGS. 4A-4D. For example, as illustrated in FIG. 4A, tip 350 can include a distal tip edge 352, an external thread 354, and a proximal tip edge 356. In some cases, as shown in FIG. 4B, tip 350 can have a length N within a range from about 0.10 inch to about 0.50 inch. Optionally, tip 350 can have a length N of about 0.30 inch. In some cases, distal tip edge 352 can have a length O within a range from about 0.01 inch to about 0.10 inch. Optionally, distal tip edge 352 can have a length O of about 0.05 inch. In some embodiments, external thread 354 can have a length P within a range from about 0.08 inch to about 0.21 inch. Optionally, external thread 354 can have a length P of about 0.13 inch. In some embodiments, a distance Q between distal tip edge 352 and external thread 354 can be within a range from about 0.01 inch to about 0.03 inch. Optionally, distance Q can be about 0.02 inch. In some cases, proximal tip edge 356 can have a length R within a range from about 0.05 inch to about 0.15 inch. Optionally, proximal tip edge 356 can have a length R of about 0.10 inch. In some embodiments, threaded section 354 can have a major thread diameter S within a range from about 0.095 inch to about 0.295 inch. Optionally, major thread diameter S can be about 0.195 inch. In some embodiments, threaded section 354 can have a minor thread diameter T within a range from about 0.075 inch to about 0.275 inch. Optionally, minor thread diameter T can be about 0.175 inch. In some cases, an outer diameter of proximal tip edge 356 will be approximately equivalent to minor thread diameter T. Typically, distal tip edge 352 includes an end 353 that is blunt or is otherwise configured to be sufficiently smooth so as to not cut tissue when applied thereto under normal operating conditions. As depicted in FIG. 4C, distal tip edge 352 can have an outer diameter U within a range from about 0.090 inch to about 0.296 inch. Optionally, outer diameter U can be about 0.196 inch. In some embodiments, proximal tip edge 356 can have an inner diameter V within a range from about 0.065 inch to about 0.265 inch. Optionally, inner diameter V can be about 0.165 inch. As illustrated in FIG. 4D, threaded section 354 can define a thread depth W and a thread pitch X. In some cases, thread depth W can be within a range from about 0.005 inch to about 0.015 inch. Optionally, thread depth W can be about 0.010 inch. In some cases, thread pitch X can be within a range from about 0.010 inch to about 0.030 inch. Optionally, thread pitch X can be about 0.020 inch. In some cases, threaded section 354 can have a thread count within a range from about 10 threads per inch to about 60 threads per inch. Optionally, threaded section 354 can have a thread count of about 40 threads per inch.

Figure 5A:
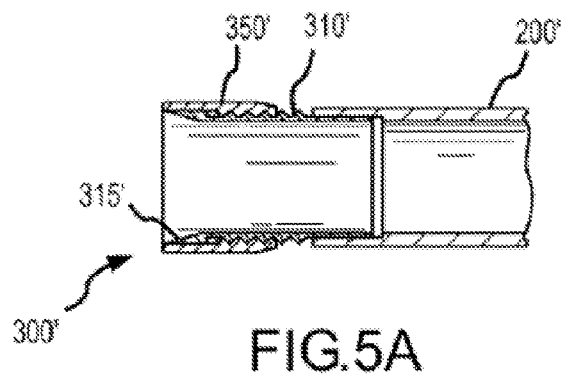
FIGS. 5A-5D show separating assemblies according to embodiments of the present invention.

FIG. 5A illustrates a separating assembly 300' according to one embodiment of the present invention, coupled with sheath 200'. Separating assembly 300' includes a separator 310' and a tip 350'. The separating assembly 300' shown in FIG. 5A is similar in some respects to the separating assembly 300 shown in FIG. 2. However, FIG. 5A depicts separator 310' coupled with sheath 200', whereas FIG. 2 depicts tip 350 coupled with sheath 200. Moreover, FIG. 5A shows tip 350' external to separator 310', whereas FIG. 2 shows separator 310 external to tip 350. In some embodiments, sheath 200' is integral with separator 310', such that separator 310' represents a distal end of sheath 200'. Depending on whether an embodiment includes a separating assembly 300 as shown in FIG. 2 or a separating assembly 300' as shown in FIG. 5A, certain features or elements of the respective tips (350, 350') or separator (310, 310') may vary. For example, a separating assembly may include a contact region for contacting a tissue or surface of a patient's body, as further discussed elsewhere herein. This contact region may be disposed on a tip or a separator of a separating assembly. In the embodiment shown in FIG. 2, the contact region is typically disposed on a surface of separator 310. In the embodiment shown in FIG. 5, the contact region is typically disposed on a surface of tip 350'. Separator 310, 310' can include a serrated or angled surface for separating. When in the undeployed configuration, the separator is typically flush with or disposed proximal to the distal end of the tip. When separator is mated with tip in this manner, the separating assembly provides for a smooth tapered, non-separating profile. In some embodiments, an undeployed configuration can refer to a separating assembly having an unexposed separator blade or a non-separating profile. When in the deployed configuration, the separator can be extended distally beyond the distal end of the tip. In some embodiments, a deployed configuration can refer to a separating assembly having an exposed separator blade or a cutting profile. In some deployed configurations, the separator is extended past the tip by about 0.5 mm to about 5 mm. In some embodiments, a separator, which may include a cutter, a stripper, or a dilator, may extend past the tip by about 1.5 mm. In some embodiments, the shape of the separator extending past or configured relative to the tip can vary or be non symmetric around a circumference of the separator. Exemplary separating assembly configurations are described in previously incorporated U.S. patent application Ser. No. 11/615,005, filed Dec. 22, 2006 (Tissue Separating Systems and Methods). Relative movement between the tip and separator can be controlled by one or more stops. For example, as shown in FIG. 2, stop 355 can prevent or inhibit separator 310 from extending distally from tip 350 beyond a certain distance. Similarly, as shown in FIG. 5A, stop 315' can prevent or inhibit tip 350' from extending distally from separator 310' beyond a certain distance.

Figure 5B:
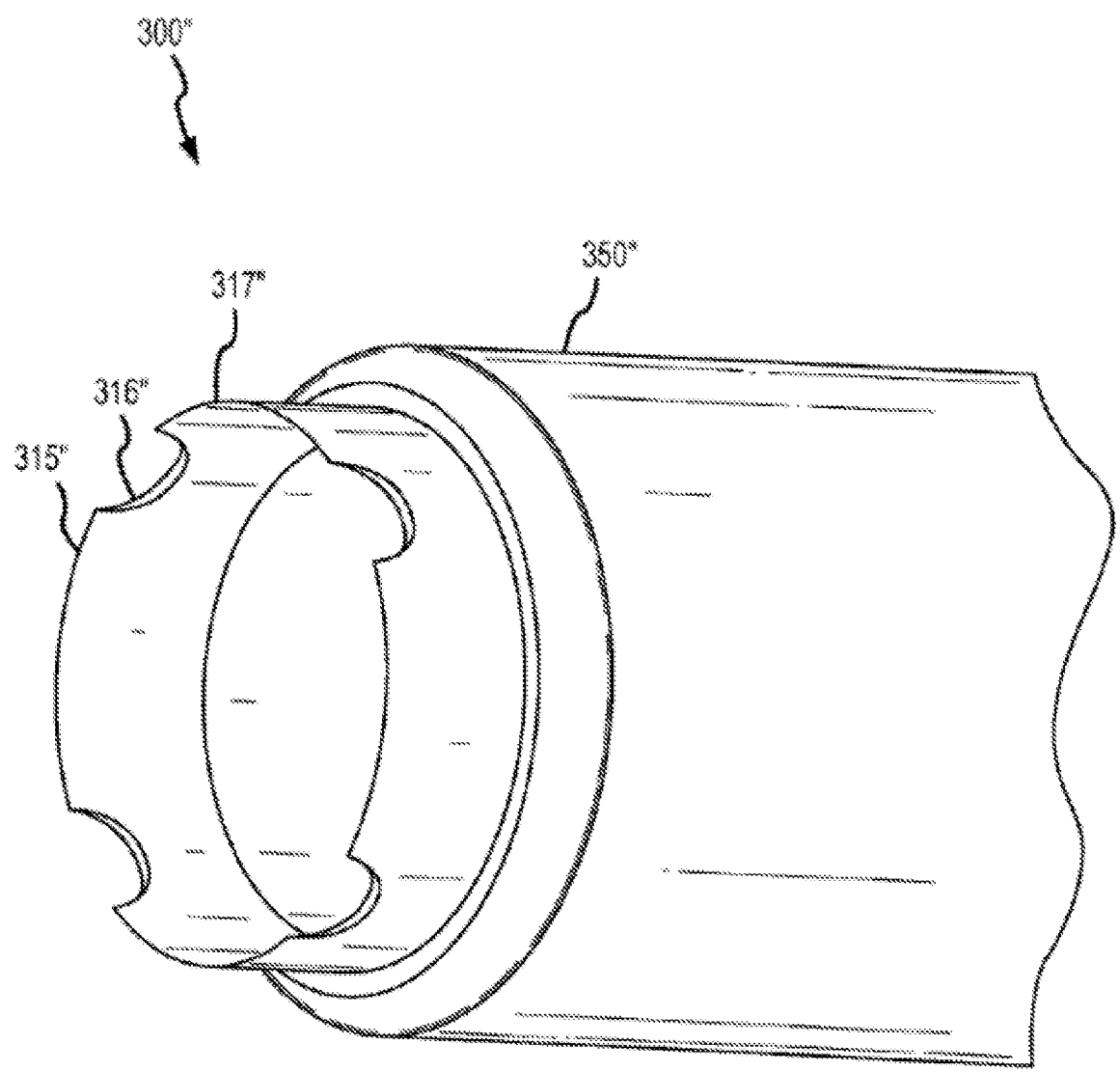
Figure 5C:
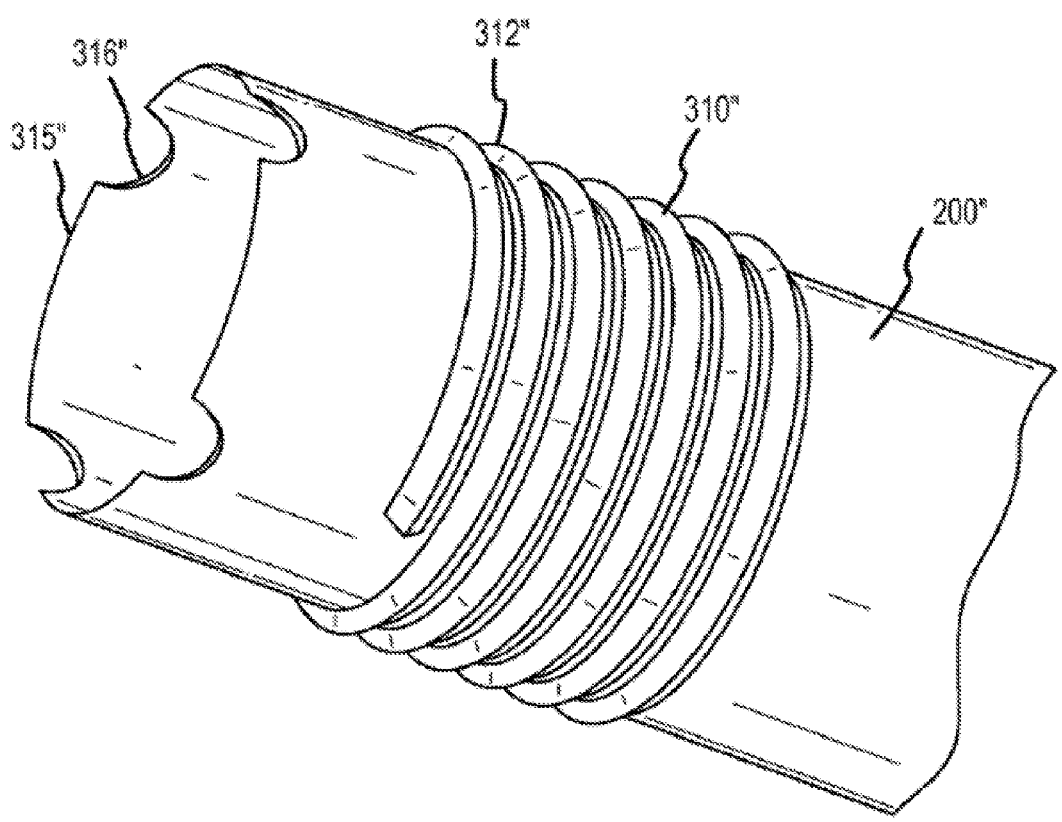
Figure 5D:
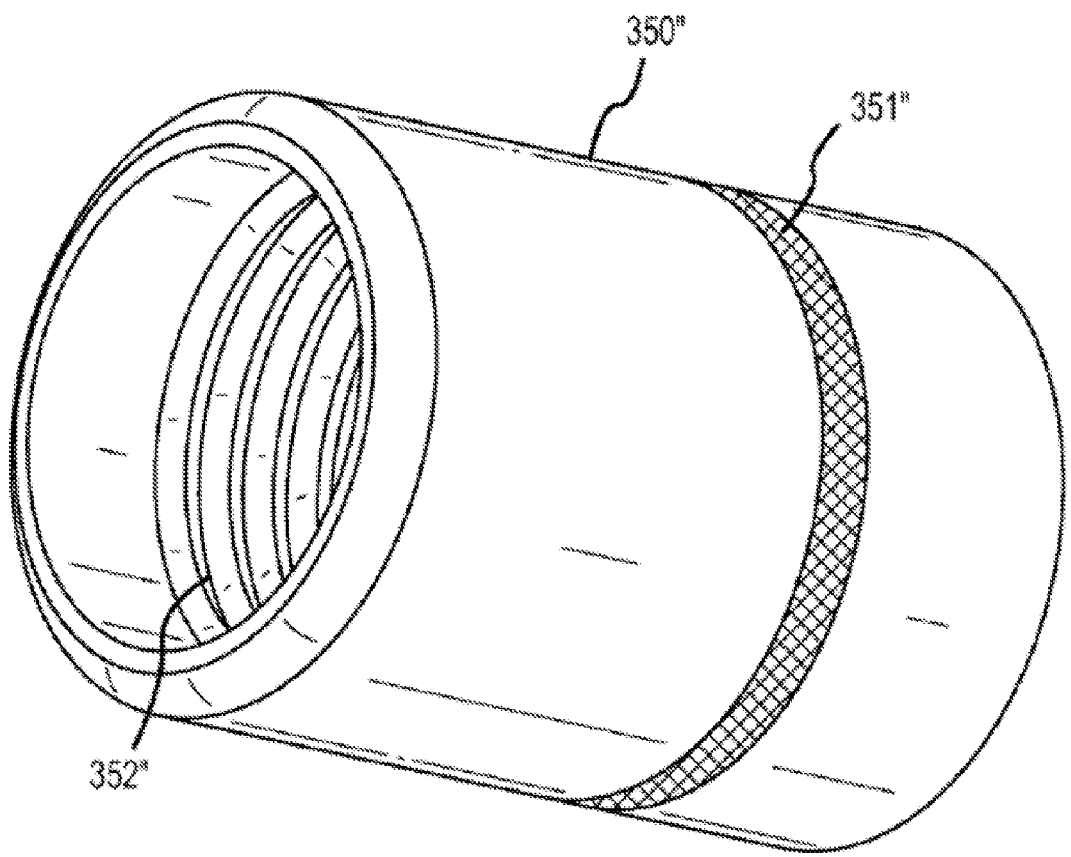

FIGS. 5B-D illustrate a separating assembly 300" according to embodiments of the present invention. Separating assembly 300" includes a separator 310" and a tip 350", and can be coupled with a sheath 200". As shown here, tip 350" is disposed external to separator 310". In some embodiments, sheath 200" is integral with separator 310", such that separator 310" represents a distal end of sheath 200". Tip 350" includes a contact region 351" for contacting a tissue or surface of a patient's body. Contact region 351" may be disposed at any suitable location on tip 350". For example, contact region 351" can be located at a proximal portion of tip 350", a medial portion of tip 350", or at a distal portion, edge, or face of tip 350". Cutter 310" can include separating edge 315" having one or more notches 316" or serrations 317". Separator 310" and tip 350" can be engaged in any of a variety of ways. For example, separator 310" can include threads 312" that interface with threads 352" of tip 350". When in the undeployed configuration, the separator is typically flush with or disposed proximal to the distal end of the tip. When separator is mated with tip in this manner, the separating assembly provides for a smooth tapered, non-separating profile. When in the deployed configuration, as shown in FIG. 5B, the separator is typically extended distally beyond the distal end of the tip.

Figure 6B:
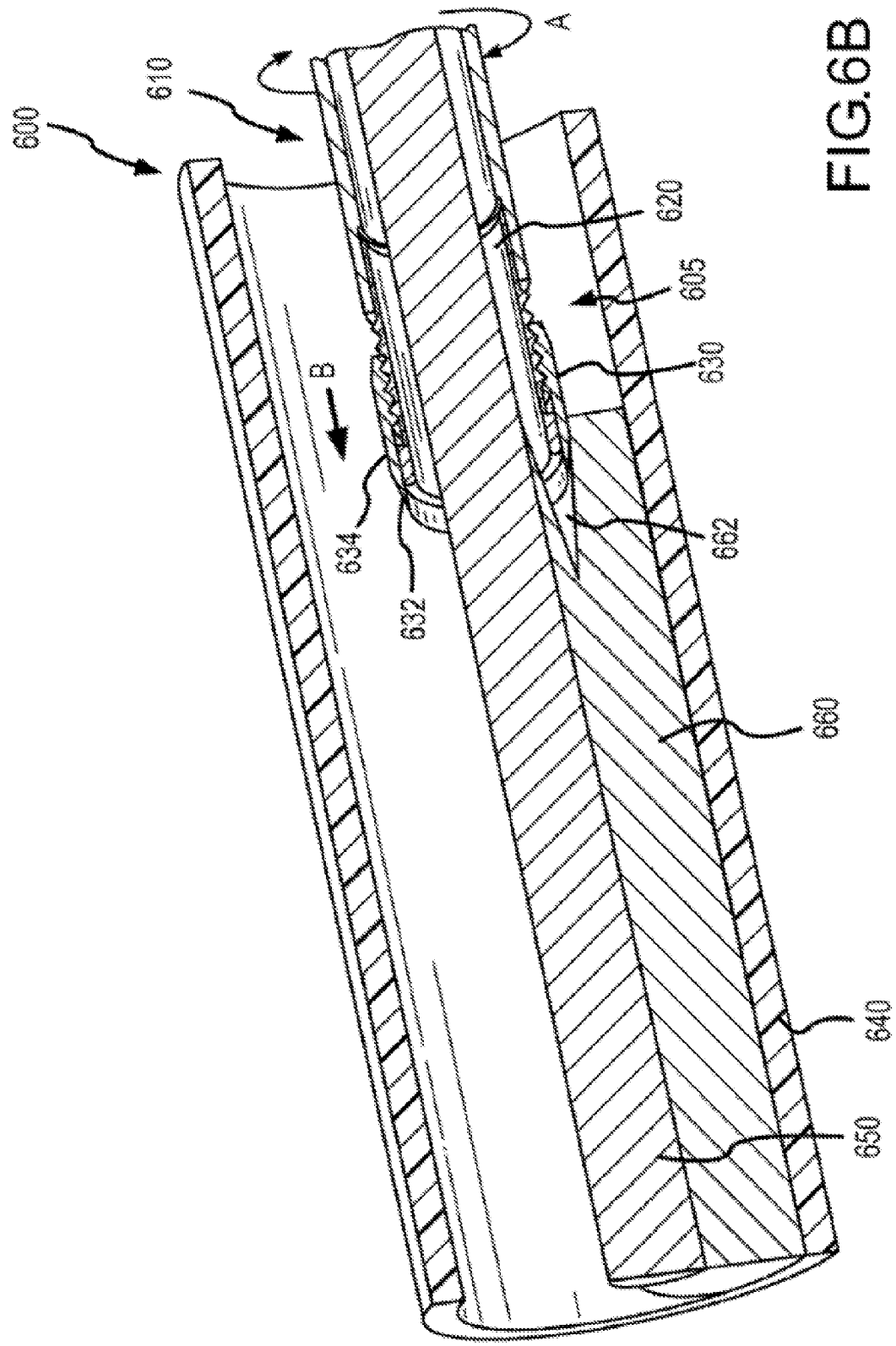
Figure 6C:
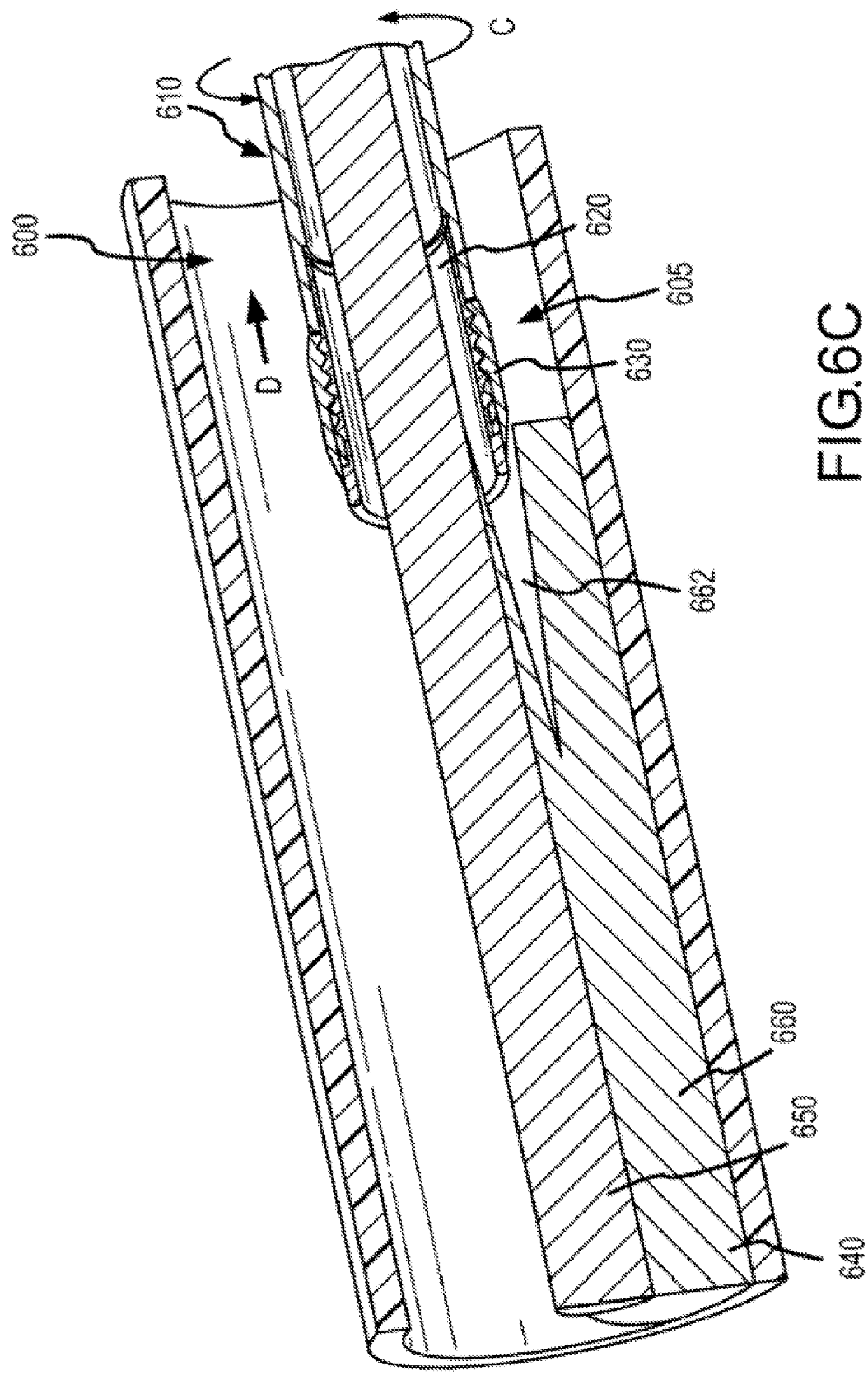

FIGS. 6A-6C illustrate a method of using a cutting assembly according to embodiments of the present invention. As shown in FIG. 6A, cutting system 600 includes a sheath 610 coupled with a tip 620, and a separator 630 engaged with tip 620. Separator 630 and tip 620 may collectively be referred to as cutting assembly 605. A cylindrical portion of separator 630 is disposed in concentric arrangement with a cylindrical portion of tip 620. Sheath 610 can include any of a variety of flexible materials, and typically includes a passage extending there through. In some embodiments, sheath 610 is sufficiently flexible to navigate tortuous paths within various body lumens or vessels. Cutting system 600 is advanced along the interior of patient vessel or lumen 640, and over the surface of pacing lead or object 650. As shown in this illustration, separator 630 is retracted from the distal end of tip 620, so as to provide a non-separating profile. It is appreciated that methods may encompass any of a variety of non-separating profiles or undeployed configurations that include an unexposed separating edge, blade, or other suitable separating means or mechanism. As separating system 600 is advanced along the object, the distal end of the system contacts the scar tissue or adhesion 660. In some cases, tissue 660 can be separated from object 650 by forcing the distal end of system 600 against tissue 660, with separating assembly 605 in a non-separating profile.

As depicted in FIG. 6B, an operator can rotate sheath 610, which in turn rotates tip 620 relative to separator 630, and thus extends separator 630 distally for cutting tissue 660. In an exemplary embodiment, the operator situates the distal end of separating system 600 so that a contact region 634 of separator 630 touches a tissue of the patient. Contact region 634 can be disposed at any location on separator 630, and is suitable for contacting a tissue or other component of or within the patient's body. Typically, contact region 634 is disposed along an external surface of separator 630. Depending on the configuration of separating assembly 605, contact region may be disposed on tip 620, as previously discussed in relation to FIGS. 2 and 5A. Friction between contact region 634 and the tissue allows tip 620 to rotate relative to separator 630, and thus the operator can extend, or retract, separator 630 or a portion thereof by rotating sheath 610. The tissue interface surface or contact region 634 can have a finish that facilitates frictional resistance. For the example, contact region 634 may include a sand blasted, grooved, coated, holed, pitted, notched, or knurled surface. The contact region surface can be pressed against the tissue surface so as to anchor or fix the contact region relative to the tissue surface or site.

Although this deployment procedure is described in terms of frictionally engaging a tissue surface with a contact region, it is understood that in some cases other mechanisms or methods can provide for relative rotational movement between the separator and tip, so as to allow the separating assembly to switch or transform between a deployed configuration and an undeployed configuration. For example, suitable combinations of knobs, gears, triggers, interior bolts, and other activating mechanisms or means can be used to cause the separator to rotate relative to the tip. It is appreciated that methods may encompass any of a variety of separating profiles or deployed configurations that include an exposed separating means or mechanism such as an edge or a blade. In some cases, the separating assembly is adapted to switch between a deployed configuration where a portion of the separating means is exposed and an undeployed configuration where the portion of the separating mechanism or means is unexposed. The portion of the separating mechanism or means may include all or some of the separating mechanism or means. Some embodiments may include temporarily fixing or releasably engaging a portion of a separating assembly with a site adjacent to or on the tissue which is to be separated. For example, a separator or tip can be temporarily fixed with a site via retractable spikes or projections disposed on an external surface of the cutter or tip. Similarly, a separator or tip can include a surface having directional projections, such as microprojections, that lay flat when the separator or tip is rotated in one direction, and stand up straight or otherwise deploy when the separator or tip is rotated in the other direction. In some cases, such projections provide a sufficiently soft and atraumatic surface so as to not cause undesired tissue damage when the device is rotated during separating operations.

As shown in FIG. 6B, the operator can rotate sheath 610 as indicated by arrow A, so as to extend or deploy separator 630 distally beyond tip 620, thus providing a separating profile for separating system 600. Separating assembly 605 can be advanced within lumen 640 as indicated by arrow B, such that distal separating edge 632 is applied to tissue 660, and makes a separation, cut, or incision 662 in tissue 660. In some embodiments, tissue 660 includes scar tissue or adhesions. In some embodiments, distal separating edge 632 is applied to tissue 660 so as to separate tissue 660 from object or lead 650 or from other tissue. In some embodiments, distal separating mechanism or edge 632 is applied to tissue 660 so as to strip tissue 660 from object or lead 650 or from other tissue. In some embodiments, distal separating edge 632 is applied to tissue 660 so as to dilate tissue 660 away from object or lead 650 or from other tissue. It is understood that in some embodiments, the distal extension of separator 630 involves rotating tip 620 in a counter-clockwise direction relative to separator 630. In other embodiments, the distal extension of cutter 630 involves rotating tip 620 in a clockwise direction relative to separator 630, depending on the orientation of the threaded arrangement between tip 620 and separator 630. The threaded interface between separator 630 and tip 620 can be designed to minimize friction and to keep out blood or tissue. The threaded mating surfaces may be polished or coated and matched to fine tolerances or other methods may be employed such as seals or greases. The pitch or count of the threads can be made to provide a known extension or retraction distance within a certain number of rotations or fractions thereof. This can allow an operator to carefully calibrate the extent to which a separating edge is deployed or undeployed via actuation of the threadable coupling between the tip and the separator.

As depicted in FIG. 6C, an operator can rotate sheath 610, which in turn rotates tip 620 relative to separator 630, and thus retracts separator 630 proximally. For example, the operator can rotate sheath 610 as indicated by arrow C, so as to retract or dispose separator 630 flush with or proximal to a distal end of tip 620, thus providing a non-separating profile for separating system 600. Accordingly, methods may include rotating the sheath to induce relative rotational movement between the separator and the tip so as to undeploy the separating means of the separator. Similarly, methods may include rotating the sheath so as to undeploy the separating assembly. Separating assembly 605 can be retracted within lumen 640 as indicated by arrow D, such that separating assembly 605 is removed from or moved proximal relative to cut or incision 662 in tissue 660. It is understood that in some embodiments, the proximal retraction of separator 630 involves rotating tip 620 in a counter-clockwise direction relative to separator 630. In other embodiments, the proximal retraction of separator 630 involves rotating tip 620 in a clockwise direction relative to separator 630, depending on the orientation of the threaded arrangement between tip 620 and separator 630.

Figure 7A:
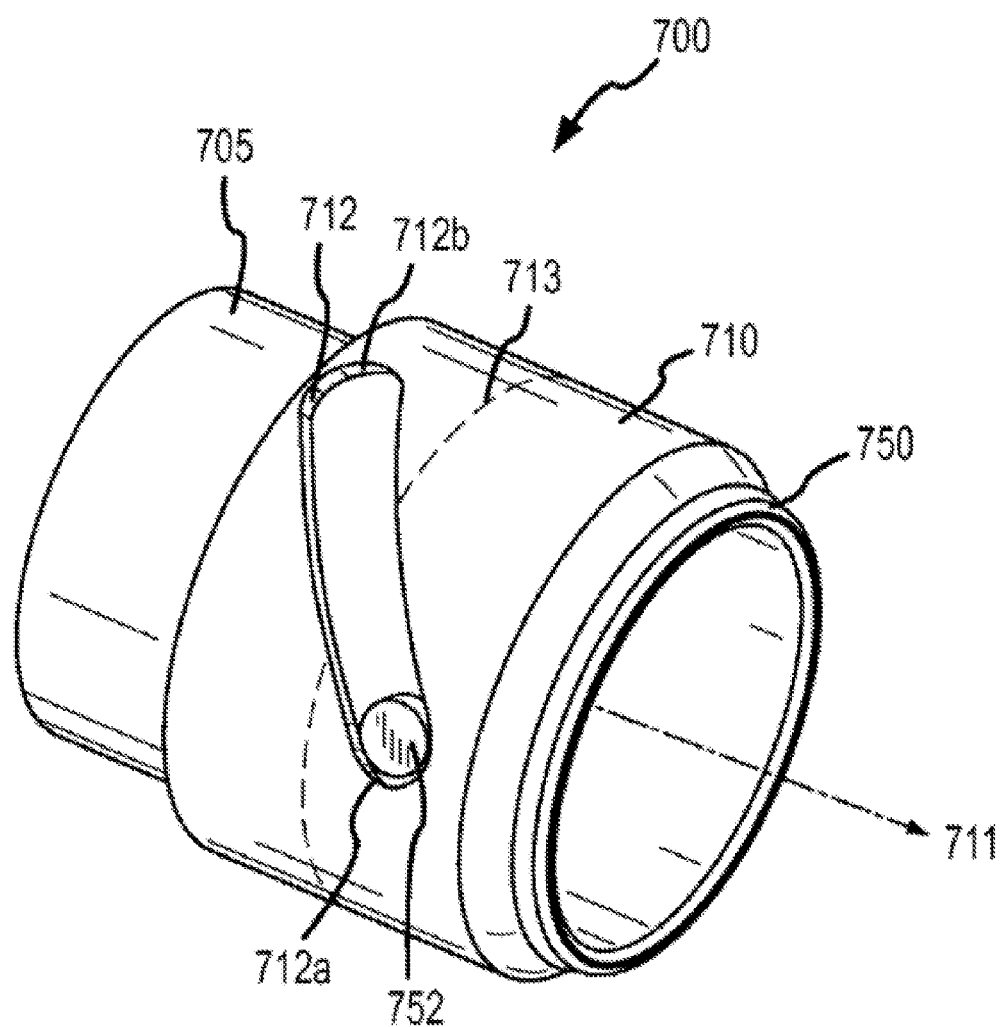
FIGS. 7A and 7B illustrate a separating assembly according to embodiments of the present invention.
Figure 7B:
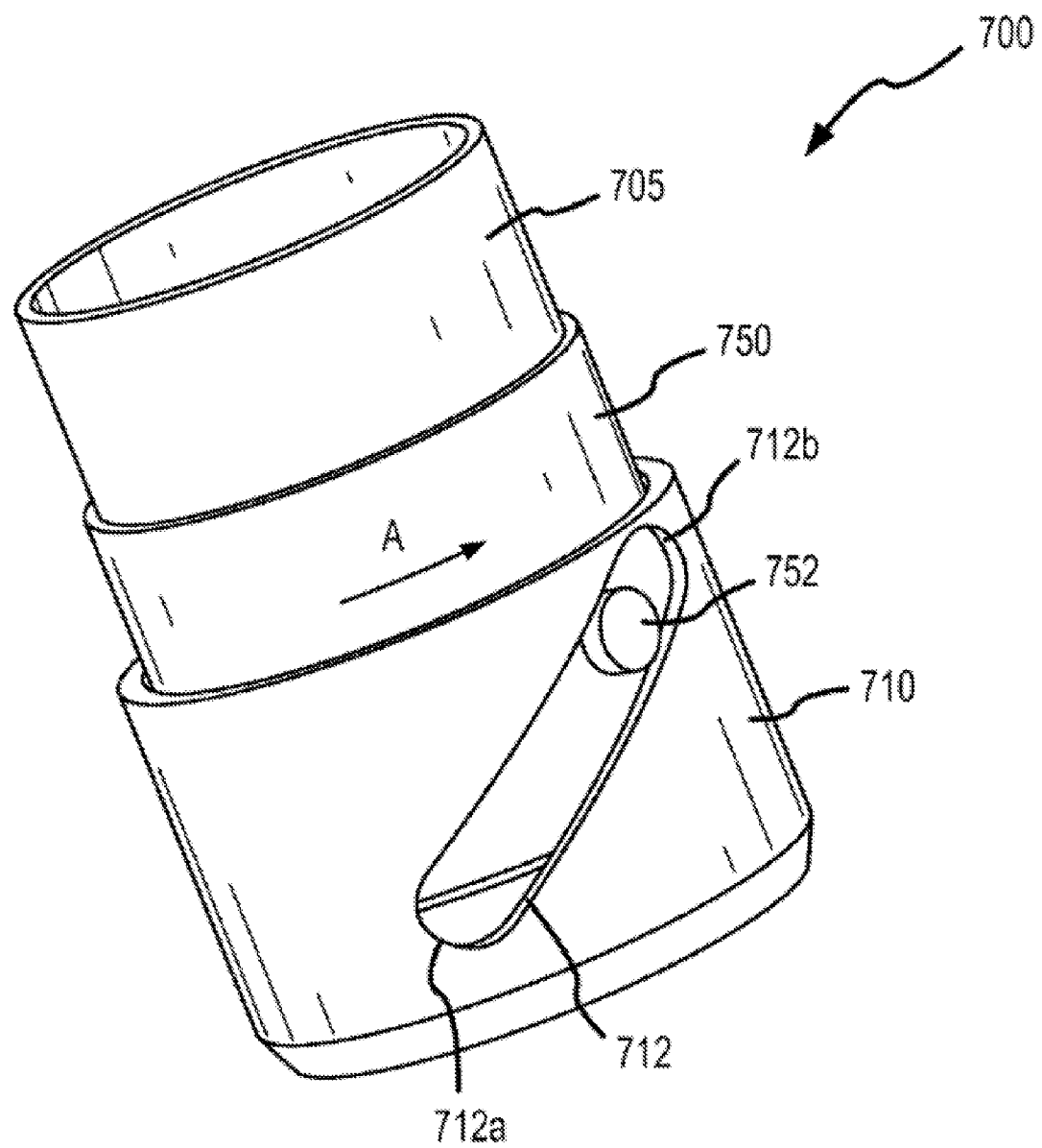

FIGS. 7A and 7B depict a separating assembly 700 according to embodiments of the present invention. Separating assembly 700 can include a separator 710 in operative association with a tip 750. Here, separator 710 includes a slot 712, and tip 750 includes a key 752. Slot 712 includes a first end 712a disposed toward a distal portion of cutter 710, and a second end 712b disposed proximal to first end 712a. Key 752 cooperatively engages slot 712, and slot 712 is aligned at an angle offset from a central longitudinal axis 711 or a circumferential band 713 of separator 710, such that when cutter 710 is rotated relative to tip 750 in one direction, key 752 is disposed more closely to first end 712a of the slot, as shown in FIG. 7A. Conversely, when separator 710 is rotated relative to tip 750 in the opposite direction, key 752 is disposed more closely to second end 712b of the slot, as shown in FIG. 7B. In some embodiments, the offset angle can be selected or calibrated to allow a user to carefully adjust the distance which the separator is extended or retracted, by correlating a movement in linear distance with a rotational movement of the sheath. Any of a variety of slot and key configurations or connections are contemplated. In some cases, the separator includes a key, and the tip includes a slot. A separating assembly may include a tip disposed at least partially within a separator, or a separator disposed at least partially within a tip. In either case, the tip may include a key, a slot, or both, and the separator may include a slot, a key, or both. In some embodiments, sheath 705 is integral with tip 750, such that tip 750 represents a distal end of sheath 705. In some embodiments, a distal end of sheath 705 is fixed with tip 750. When initially placed within a vessel or lumen of a patient, separating assembly 700 is typically disposed in an undeployed configuration, as shown in FIG. 7A, whereby a distal end of separator 710 is flush with or proximal to a distal end of tip 750. Once the assembly 700 is positioned at or near a tissue which an operator wishes to separate, the operator can maneuver the assembly 700 so that an external surface of separator 710 frictionally contacts a tissue surface of the patient. The operator can then rotate shaft 705 so that tip 750 rotates relative to separator 710 as shown by arrow A, thus extending a portion of separator 710 distally beyond tip 750, as shown in FIG. 7B. The separating assembly 700 is thus in a deployed configuration and ready for separating the desired tissue.

Figure 8A:
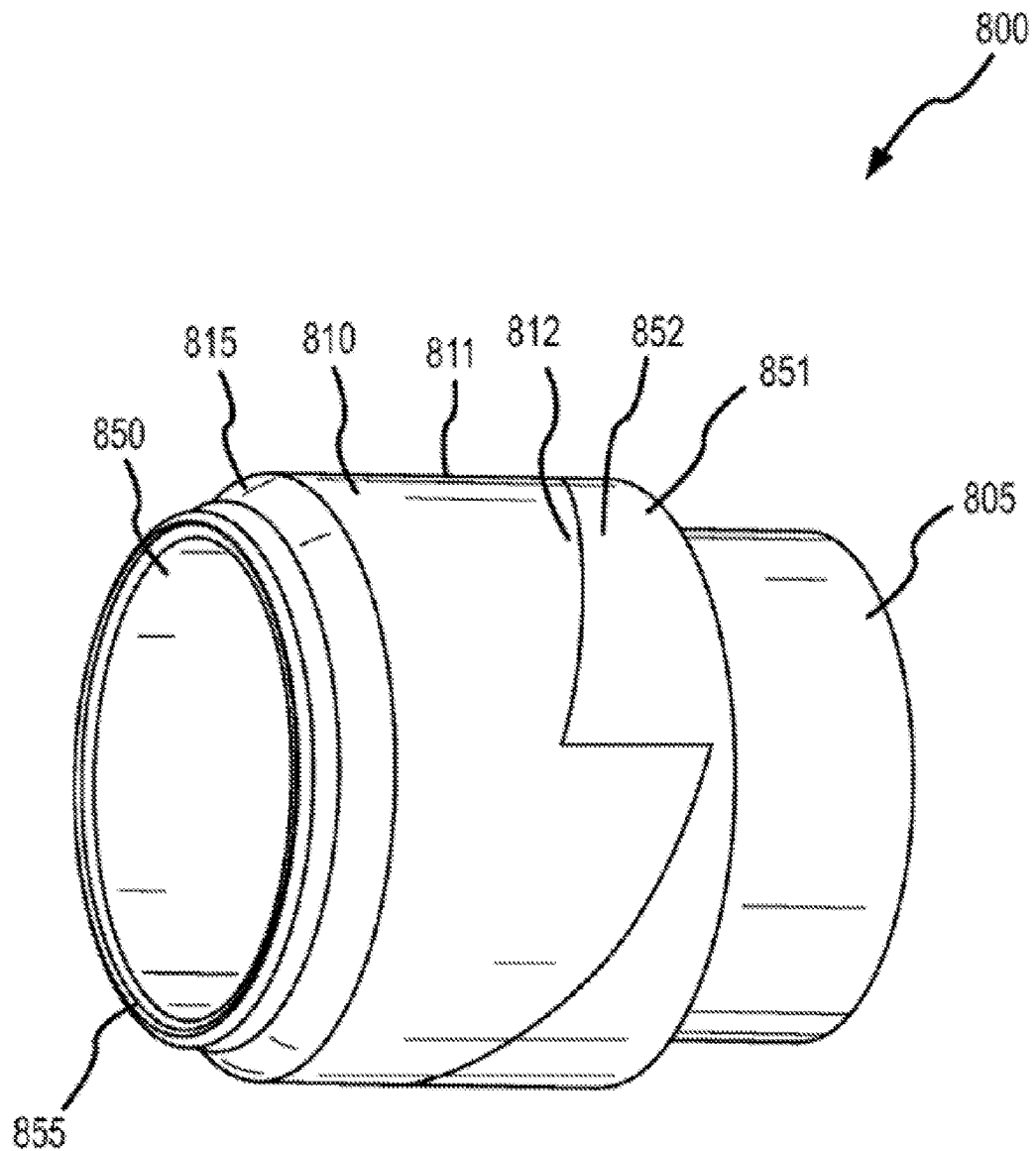
FIGS. 8A-8C depict a separating assembly according to embodiments of the present invention.
Figure 8B:
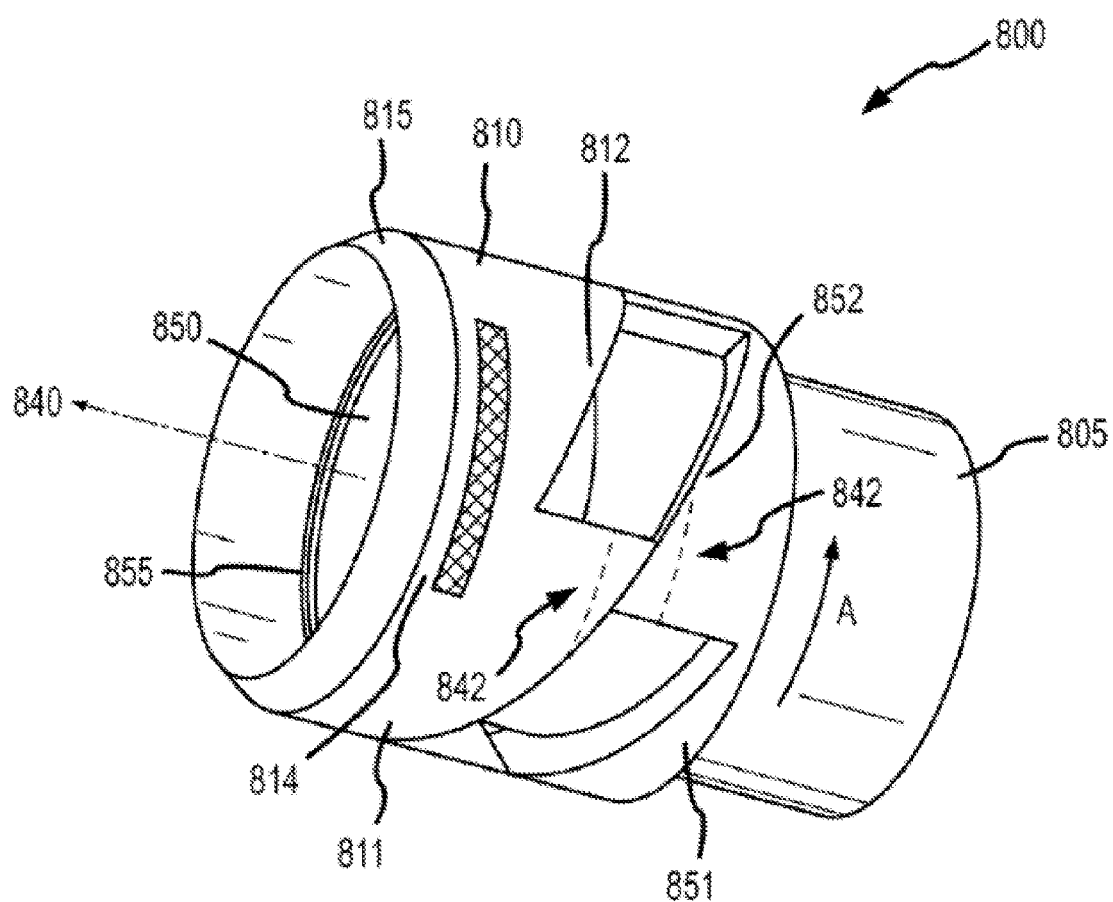
Figure 8C:
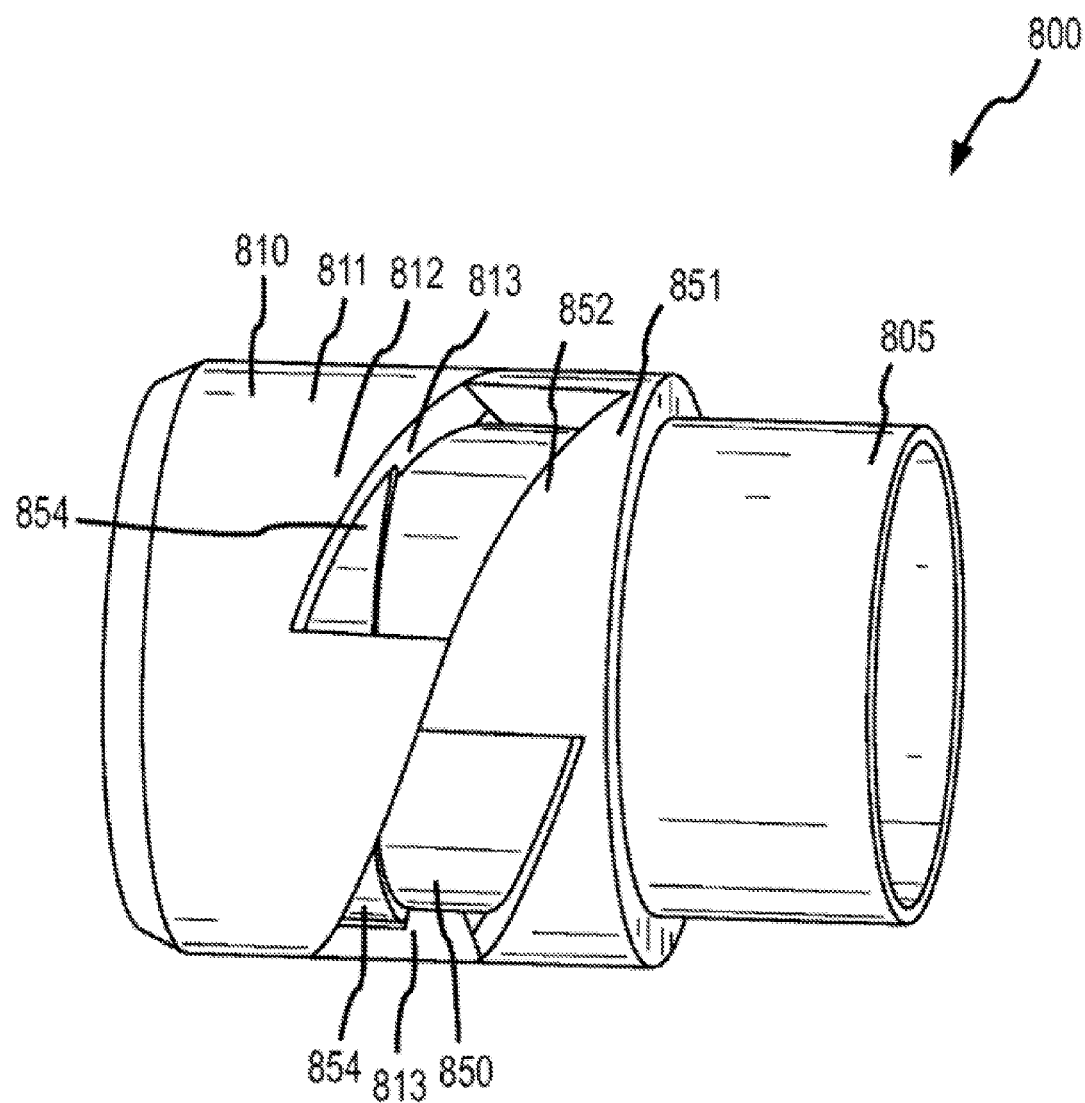

FIGS. 8A-8C depict a separating assembly 800 according to embodiments of the present invention. Separating assembly 800 can include a separator 810 in operative association with a tip 850. For example, separator 810 can be coupled with tip 850 via a cam connection. In some cases, separator 810 includes distal cam 811 having a distal cam interface 812, and tip 850 or sheath 805 includes a proximal cam 851 having a proximal cam interface 852. Distal cam interface 812 and proximal cam interface 852 are cooperatively engaged such that relative rotational movement between distal cam 811 and proximal cam 851 is associated with relative linear movement between distal cam 811 and proximal cam 851. In this way, relative rotation of the cams 811, 851 can cause the separator 810 to extend and retract relative to tip 850. In some configurations, the cam interfaces provide an angled profile. Optionally, the cam interfaces can provide a curved or eccentric profile. An angled or curved profile can be designed or calibrated to allow a user to carefully adjust the distance which the separator is extended or retracted, by correlating a movement in linear distance with a rotational movement of the sheath. Thus, an operator can control the extent to which a separating edge or means is deployed or undeployed via actuation of the cam coupling between the tip and the separator. FIG. 8A depicts separating assembly in an undeployed configuration, wherein a separating edge or means 815 of separator 810 is disposed flush with or proximal to a distal edge 855 of tip 850. In use, as shown in FIG. 8B, a contact region 814 of separator 810 can engage a body tissue or other surface or object within a patient, and the operator can rotate tip 850 relative to separator 810 as indicated by arrow A, so as to provide linear separation between distal cam 811 and proximal cam 852 as distal cam interface 812 and proximal cam interface 852 slide against each other. Distal cam interface 812 and proximal cam interface can be aligned at an angle offset from a central longitudinal axis 840 or a circumferential band 842 of distal cam 811 or proximal cam 851, such that when separator 810 is rotated relative to tip 850, relative linear motion between separator 810 and tip 850 is induced. In some embodiments, sheath 805 is integral with tip 850, such that tip 850 represents a distal end of sheath 805. In some embodiments, a distal end of sheath 805 is fixed with tip 850. As shown in FIG. 8B, rotational actuation of cam interfaces 812 and 852 disposes separating assembly 800 in a deployed configuration, ready for separating the desired tissue. FIG. 8C also depicts separating assembly 800 in a deployed configuration. As seen from this perspective, tip 850 can include a stop 854 configured to engage an edge or projection 813 of separator 810. Stop 854 can prevent or inhibit separator 810 from excessive or unwanted movement in the distal direction. In some cases, stop 854 prevents or inhibits separator 810 from becoming detached or disengaged from tip 850 or sheath 805.

Figure 9A:
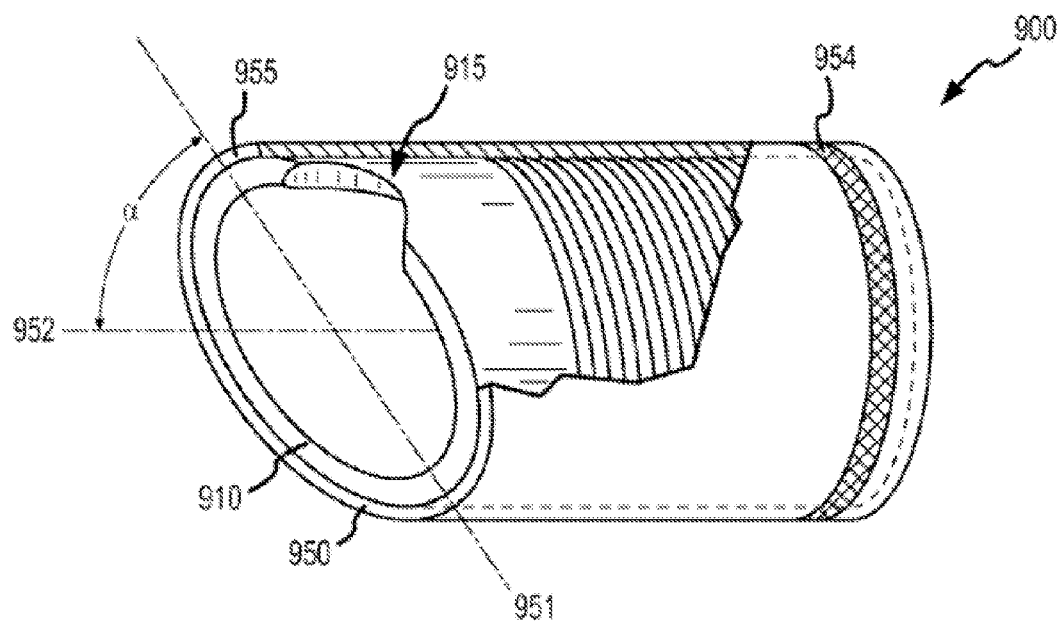
FIGS. 9A and 9B depict a separating assembly according to embodiments of the present invention.
Figure 9B:
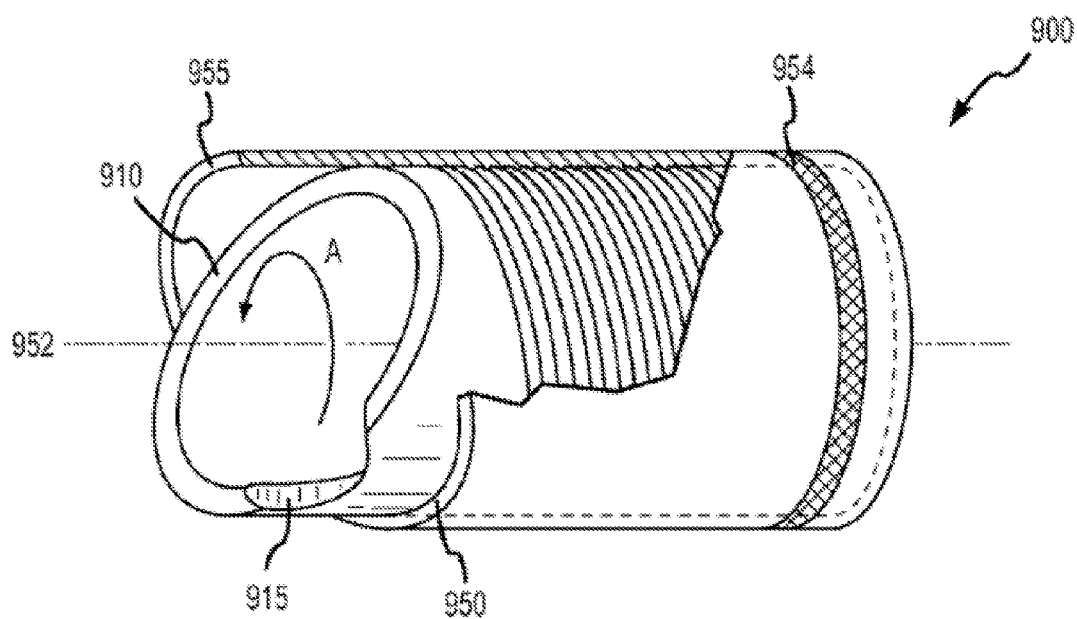

FIGS. 9A and 9B show a separating assembly 900 according to embodiments of the present invention. Separating assembly 900 can include a separator 910 in operative association with a tip 950. For example, separator 910 can be coupled with tip 950 via a threaded connection. Relative rotation between separator 910 and tip 950 can be the result of or the cause of relative positioning between separator 910 and tip 950 along a common longitudinal axis. FIG. 9A depicts separating assembly 900 in an undeployed configuration, wherein a separating edge or blade 915 of separator 910 is disposed flush with or proximal to a distal edge 955 of tip 950. A distal end or face of tip 950 is beveled so as to define a plane 951 that intersects a central longitudinal axis 952 of tip 950 at an angle α, which in some cases can be within a range from about 10 degrees to about 80 degrees. A distal end or face of separator 910 may present a similar beveled configuration. In use, a contact region 954 of tip 950 can engage a body tissue or other surface or object within a patient, and the operator can induce relative rotational movement between tip 950 and separator 910. As shown in FIG. 9B, the operator can rotate separator 910 relative to tip 950 as indicated by arrow A, so as to expose separating blade 915. In some embodiments, separating blade 915 is exposed and configured for use, and separating assembly 900 is in a deployed configuration, while separating blade 915 remains proximal to distal edge 955 of tip 950.

Figure 10A:
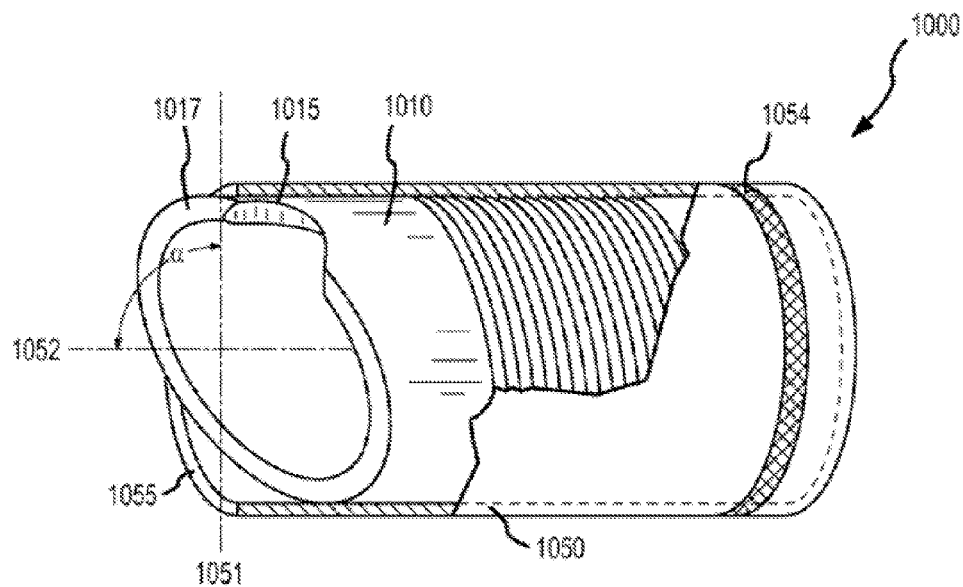
FIGS. 10A and 10B depict a separating assembly according to embodiments of the present invention.
Figure 10B:
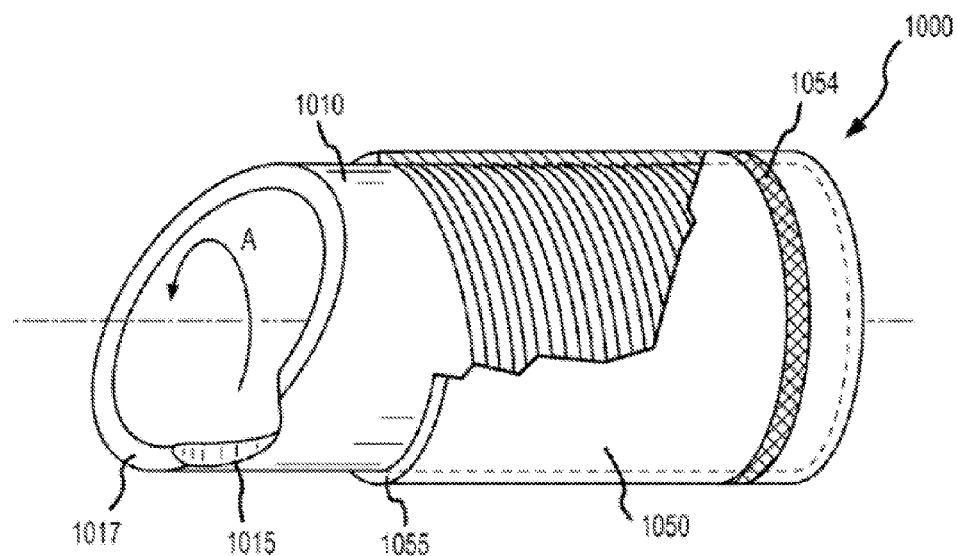

FIGS. 10A and 10B show a separating assembly 1000 according to embodiments of the present invention. Separating assembly 1000 can include a separator 1010 in operative association with a tip 1050. For example, separator 1010 can be coupled with tip 1050 via a threaded connection. Relative rotation between separator 1010 and tip 1050 can be the result of or the cause of relative positioning between separator 1010 and tip 1050 along a common longitudinal axis. FIG. 10A depicts separating assembly 1000 in an undeployed configuration, wherein a separating edge or blade 1015 of separator 1010 is disposed flush with or proximal to a distal edge 1055 of tip 1050. In some cases, a distal end or portion 1017 of separator 1010 can be positioned distal to distal tip edge 1055, when separating assembly is in the undeployed configuration and separating blade or means 1015 is unexposed. A distal end or face of tip 1050 defines a plane 1051 that perpendicularly intersects a central longitudinal axis 1052 of tip 1050. In some cases, plane 1051 intersects axis 1052 at an angle α, which in some cases can be within a range from about 75 degrees to about 90 degrees. A distal end or face of separator 1010 may present a beveled configuration as described above with reference to FIGS. 9A and 9B. In use, a contact region 1054 of tip 1050 can engage a body tissue or other surface or object within a patient, and the operator can induce relative rotational movement between tip 1050 and separator 1010. As shown in FIG. 10B, the operator can rotate separator 1010 relative to tip 1050 as indicated by arrow A, so as to expose separating blade 1015, and thus place separating assembly 1000 in a deployed configuration.

In addition to being well suited for the removal or detachment of pacing leads from a patient, embodiments of the present invention are well suited for detaching or removing any of a variety of objects from a patient, such as catheters, wires, implants, or other foreign bodies, and for separating tissue from other neighboring or adjacent tissue. Such objects may be disposed in veins, arteries, or any body lumen, cavity, or tissue.

Embodiments of the invention have now been described in detail. However, it will be appreciated that the invention may be carried out in ways other than those illustrated in the aforesaid discussion, and that certain changes and modifications may be practiced within the scope of the appended claims. Accordingly, the scope of this invention is not intended to be limited by those specific examples, but rather is to be accorded the scope represented in the following claims.

What is claimed is:

1. A separating system for detaching a pacing lead from a patient, comprising:
    a sheath having a proximal end and a distal end; and
    a separating assembly coupled with the distal end of the sheath, the separating assembly comprising a cutter having a distal cutting edge, the separating assembly further comprising an outer band having a blunt distal end, wherein at least a portion of the outer band is disposed external and coaxial to the cutter, wherein the outer band and the cutter are coupled via a slot and key configuration, thereby allowing relative rotational movement of the outer band and the cutter, wherein one of the cutter and the outer band comprises a channel of the slot and key configuration in its circumference, wherein the channel includes a first end, a second end, and a length, wherein the length of the channel extends between the first end and the second end for less than 360 degrees the circumference of the one of the cutter and the outer band;
    wherein each of the sheath, the outer band, and the cutter are configured for placement over the pacing lead;
    wherein the slot and key configuration of the separating assembly is adapted to switch between a deployed configuration where the distal cutting edge of the cutter is exposed in response to rotation of the sheath in a first direction and an undeployed configuration where the distal cutting edge of the cutter is proximal of the blunt distal end of the outer band in response to rotation of the sheath in a second direction opposite the first direction.

2. The separating system according to claim 1, wherein the cutter and the outer band are configured for relative rotational movement via the slot and key configuration, wherein at least a portion of the channel is aligned at an angle offset from a central longitudinal axis of the cutter.

3. The separating system according to claim 1, wherein the other of the cutter and the outer band comprises a key of the slot and key configuration, and wherein the key is movably received in the channel.

4. The separating system according to claim 1, wherein in the deployed configuration the distal cutting edge of the cutter extends past the outer band a distance in the range from about 0.5 mm to about 3 mm.

5. The separating system according to claim 1, wherein the distal cutting edge includes a plurality of serrations.

6. The separating system according to claim 1, wherein the distal cutting edge is beveled relative to a central longitudinal axis of the cutter.

7. The separating system according to claim 1, wherein the distal cutting edge defines a plane that intersects with a central longitudinal axis of the cutter at an angle of about 10 degrees to about 80 degrees.

8. A separating system for detaching an object from a patient, comprising:
    a sheath having a proximal end and a distal end; and
    a separating assembly coupled with the distal end of the sheath, the separating assembly comprising an outer band having a blunt distal edge, the separating assembly further comprising a cutter having a distal cutting edge and a portion that is coaxial with the outer band;
    wherein the cutter and the outer band are coupled via a slot and key configuration, thereby allowing relative rotational movement of the outer band and the cutter, wherein one of the cutter and the outer band comprises a channel of the slot and key configuration in its circumference, wherein the channel includes a first end, a second end, and a length, wherein the length of the channel extends between the first end and the second end for less than 360 degrees the circumference; and
    wherein the slot and key configuration facilitates switching between a deployed configuration where a portion of the cutter is exposed and an undeployed configuration where the portion of the cutter is unexposed.

9. The separating system according to claim 8, wherein the cutter and the outer band are configured for relative rotational movement via the slot and key configuration, wherein at least a portion of the channel is aligned at an angle offset from a central longitudinal axis of the cutter.

10. The separating system according to claim 8, wherein the other of the cutter and the outer band comprises a key of the slot and key configuration, and wherein the key is movably received in the channel.

11. The separating system according to claim 8, wherein in the deployed configuration the distal cutting edge of the cutter extends past the outer band a distance in the range from about 0.5 mm to about 3 mm.

12. The separating system according to claim 8, wherein the distal cutting edge includes a plurality of serrations.

13. The separating system according to claim 8, wherein the distal cutting edge is beveled relative to a central longitudinal axis of the cutter.

14. The separating system according to claim 8, wherein the distal cutting edge defines a plane that intersects with a central longitudinal axis of the cutter at an angle of about 10 degrees to about 80 degrees.

15. A separating system for detaching a pacing lead from a patient, comprising:
a sheath having a proximal end and a distal end; and
a separating assembly coupled with the distal end of the sheath, the separating assembly comprising an outer band having a blunt distal end that is configured without a cutting edge, and the separating assembly further comprising a cutter having a distal cutting edge and disposed at least partially within the outer band, wherein the outer band and the cutter are coupled via a slot and key configuration, thereby allowing relative rotational movement of the outer band and the cutter, wherein the cutter comprises a channel of the slot and key configuration in its circumference, wherein the channel includes a first end, a second end, and a length, wherein the length of the channel extends between the first end and the second end for less than 360 degrees the circumference of the cutter;
wherein each of the sheath, the outer band, and the cutter are configured for placement over the pacing lead; and
wherein the slot and key configuration of the separating assembly allows the separating assembly to switch between a deployed configuration where the distal cutting edge of the cutter is exposed distally past the blunt distal end of the outer band in response to rotation of the sheath in a first direction and an undeployed configuration where the distal cutting edge of the cutter is proximal of the blunt distal end of the outer band in response to rotation of the sheath in a second direction opposite the first direction.

16. The separating system according to claim 15, wherein the cutter and the outer band are configured for relative rotational movement via the slot and key configuration, wherein at least a portion of the channel is aligned at an angle offset from a central longitudinal axis of the cutter.

17. The separating system according to claim 15, wherein in the deployed configuration the distal cutting edge of the cutter extends past the outer band a distance in the range from about 0.5 mm to about 3 mm.

18. The separating system according to claim 15, wherein the distal cutting edge includes a plurality of serrations.

19. The separating system according to claim 15, wherein the distal cutting edge is beveled relative to a central longitudinal axis of the cutter.

20. The separating system according to claim 15, wherein the distal cutting edge defines a plane that intersects with a central longitudinal axis of the cutter at an angle of about 10 degrees to about 80 degrees.

* * * * *